US008489414B2

(12) United States Patent
McEachern

(10) Patent No.: US 8,489,414 B2
(45) Date of Patent: *Jul. 16, 2013

(54) PHYSICIAN OFFICE VIEWPOINT SURVEY SYSTEM AND METHOD

(76) Inventor: J. Edward McEachern, Boise, ID (US)

( * ) Notice: Subject to any disclaimer, the term of this patent is extended or adjusted under 35 U.S.C. 154(b) by 839 days.

This patent is subject to a terminal disclaimer.

(21) Appl. No.: 12/394,659

(22) Filed: Feb. 27, 2009

(65) Prior Publication Data

US 2009/0222284 A1 Sep. 3, 2009

Related U.S. Application Data

(63) Continuation of application No. 10/008,027, filed on Nov. 5, 2001, now Pat. No. 7,552,063.

(60) Provisional application No. 60/245,752, filed on Nov. 3, 2000.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................... 705/2–3; 600/300
See application file for complete search history.

(56) References Cited

U.S. PATENT DOCUMENTS

| 4,345,315 A | 8/1982 | Cadotte et al. |
| 5,365,425 A | 11/1994 | Torma et al. |
| 5,544,044 A | 8/1996 | Leatherman |
| 5,652,842 A * | 7/1997 | Siegrist et al. .................... 705/2 |
| 5,706,441 A | 1/1998 | Lockwood |
| 5,909,669 A | 6/1999 | Havens |
| 5,924,073 A | 7/1999 | Tyuluman et al. |
| 5,961,332 A | 10/1999 | Joao |
| 6,151,581 A * | 11/2000 | Kraftson et al. .................. 705/3 |
| 6,283,761 B1 * | 9/2001 | Joao .............................. 434/236 |
| 6,301,586 B1 | 10/2001 | Yang et al. |

(Continued)

FOREIGN PATENT DOCUMENTS

JP 2002007660 A 1/2002

OTHER PUBLICATIONS

Anonymous. "Patient Satisafaction Survey", Oct. 2000. Trustee. vol. 53, Issue 9, p. 24.

(Continued)

*Primary Examiner* — Robert Morgan
*Assistant Examiner* — Rajiv Raj
(74) *Attorney, Agent, or Firm* — Pearne & Gordon LLP

(57) ABSTRACT

A system and method for conducting surveys, and, more particularly, an at least partially automated and efficient system and method for collecting, processing, and displaying customer satisfaction survey information that enables a product or service provider to evaluate the quality of goods and/or services received based on ratings and reports obtained by performing surveys of customers, employees, and/or staff. The system utilizes an execution platform using a clinical process improvement methodology. The system provides the execution platform with software scripts implementing the clinical improvement process, using drill-down questioning techniques and verbatim comments tailored to the survey participants comments and/or status information to gain insights into the participants' reasons for their opinions. The system obtains raw survey data and processes that data into useful survey information, such as graphs and charts, for presenting to survey consumers (i.e., system users) who may be remotely located. In this way the system and method can be utilized in a quality improvement program for any service or product provider.

28 Claims, 11 Drawing Sheets

U.S. PATENT DOCUMENTS

| | | |
|---|---|---|
| 6,330,710 B1 | 12/2001 | O'Neil et al. |
| 6,381,576 B1 | 4/2002 | Gilbert |
| 6,381,604 B1 | 4/2002 | Caughran et al. |
| 6,442,714 B1 | 8/2002 | Griffin et al. |
| 6,564,259 B1 | 5/2003 | Baber et al. |
| 6,618,746 B2 | 9/2003 | Desai et al. |
| 6,625,647 B1 | 9/2003 | Barrick, Jr. et al. |
| 6,647,410 B1 | 11/2003 | Scimone et al. |
| 6,826,540 B1 | 11/2004 | Plantec et al. |
| 2001/0044809 A1 | 11/2001 | Parasnis |
| 2002/0065926 A1 | 5/2002 | Hackney |

OTHER PUBLICATIONS

"CustomerCast Subscriber Satisfaction System Provides a Powerful Competitive Advantage for Excite@Home", PR Newsire. New York: Nov. 18, 1999, p. 1.

Czarnecki, Mark T., "Benchmarking Can Add Up for Healthcare Accounting", Sep. 1994, Healthcare Financial Management. vol. 48, Issue 9, p. 62.

Eubanks, Paula. "CEOs Cite Job Satisfaction; Experts See Risks", Jun. 20, 1991. Hospitals, vol. 65, Issue 12, p. 62.

Fisher, Charles R., "Trends in Total Hospital Financial Performance Under the Prospective Payment System", Spring 1992, Health Care Financing Review, vol. 13, Issue 3, p. 1.

Gregory, Nancy and Kaldenberg, Dennis O., "Satisfaction With the Billing Process: Using a Patient Survey to Identify Opportunities for Process Improvement", Summer 2000, Hospital Topics, vol. 78, Issue 3, p. 20.

Sloan, Stanley, "Health Care CEO Survey", Dec. 1992, Georgia Trend, vol. 8, Issue 4, p. 45.

Mowll, Charles A., "Hospitals Rate Fiscal Intermediary Performance", Mar. 1989, Healthcare Financial Management, vol. 43, Issue 3, p. 110.

Giunipero, Larry C. and Stephina, Lee. "Job Status and Satisfaction of Hospital Material Managers", Feb. 1987, Hospital Material Management Quarterly, vol. 8, Issue 3, and p. 66.

* cited by examiner

FIGURE 9

Health Assets

| Function | Habit | Knowledge | Prevention |
|---|---|---|---|
| Daily<br>no difficulties<br>Feeling<br>slight problem<br>Social<br>no limitations<br>Pain<br>no pain<br>Social<br>quite a lot<br>Physical<br>very healthy | Good Health<br>does not drink<br>does not smoke<br>wears seat belts | | Has enough money<br>Had low cholesterol |

Health Needs

| Patient | Clinical | Suggested | Reading & Education |
|---|---|---|---|
| Function | | more exercise<br>loose weight<br>eat well | |
| Symptom | | | |
| Concerns /<br>FamHx<br>exercise &<br>needs | | | Risk |
| Habit<br>told to reduce<br>alcohol | | | |
| Prevention<br>no education<br>about STDs<br>OCPs | | | Other |

Health Information | Personal Value Compass Initial Summery

Patient        <name>                <picture here>          Age:
SSN            000-00-000                                    Gender:
Date of Birth  mm-dd-yyyy                                    Race:
clinican                                                     ht / wt
visit type:    Initial                                       BMI:

History

Current Problem areas
Past problema and Surgenes:
Providers seen in last 6 months:
Treatments in the last 6 months:

Functional Status

Pain and Daily Activity

| Activity | Impact of pain Initial Visit / This Visit |
|---|---|
| Dressing | 2-slight |
| Lifting | 3-moderate |
| Walking | 4-substantial |
| Sitting | 5-severe |
| Standing | 2-slight |
| Sleeping | 1-none |
| Social Life | 4-substantial |
| Traveling | 2-slight |
| Sex Life | 4-subsatntial |
| ODI | 61 |
| Oswestry Disability Index (0-100) | |

SF-36

Initial visit  ▓ this visit bar chart: 0–100 scale across: bodily pain, general health, mental health, physical function, role emotional, role physical, social function, vitality

Work Status
Work Status:      currently working
hours / week:     80-120
all days / last 180:  3 summary scales (100/80/60): MCS <t2>, PCS <t2>

FIGURE 10A

Satisfaction

Expectations from Treatment expectations met?
how likely?

Sx relief
Activities
Sleep
Work life
Exercise

Satisfaction:
With treatment to date?
choose same provider again?

Costs

Work Missed due to illness last 180 days:          6 days
Financial assistance
Insurance:              no
Social Security:        na
Disability              na
Workers comp:           na

Clinical Status

Other Problems
1 Hypertension
2
3
4

Screening              frequency
Smoking Now
Duration?
Last Pap Smear?        1-3 years
Last SBE               1-2 years
Mammogram              1-2 years
Stool Guiac            1 yrs
Sigmoidoscopy          5 years
Tetanus toxoid         10 years
Influenza vaccine      1 years
Pneumovax              once
Cholestrol             *
Medications   Medications
HCTZ 50mg BID  01 / 01 / 1997

Allergies      none

FIGURE 10B

PHYSICIAN OFFICE VIEWPOINT SURVEY SYSTEM AND METHOD

CROSS-REFERENCES TO RELATED APPLICATIONS

This application is a continuation of U.S. patent application Ser. No. 10/008,027 which was filed on Nov. 5, 2001, and which claims the benefit of U.S. Provisional Application Ser. No. 60/245,752, filed Nov. 3, 2000, both of which are incorporated herein by reference.

BACKGROUND OF THE INVENTION

The present invention, the Physician Office Viewpoint Survey System and Method [POVS], relates generally to a system and method for collecting and presenting information, and more particularly to a system and method for collecting, processing, and presenting information on (1) a respondent's health status; (2) respondent's experience at a health provider's location; (3) personal information about respondent (e.g., age, gender, health information); (4) a health provider's fiscal performance and (5) quality parameters based on these, and other, collection data (including other surveys and processed information).

Conventional approaches for surveying consumers of products and services, such as health care services, generally use standard survey forms or questionnaires, whereby an agent calls or visits a survey participant and performs the survey. Alternatively, the participant may be mailed a survey form for completion.

However, these methods of performing surveys are inefficient and often inaccurate. Individual agents are typically used to perform the survey, and to tally and process the results into an assessment as to how well an organization is performing. Although computers are likely to be used to analyze the survey data, human agents are still typically used to enter the data into a computer or to perform the actual survey questioning. Unfortunately, human agents are expensive to hire, increasing survey costs, and humans often make mistakes, leading to survey inaccuracies.

In traditional surveys a series of questions asked one after another in a static, sequential order. The surveys are collected, perhaps, by the respondent filling out a paper form or with a skilled questioner asking the respondent questions, with the results compiled after the survey is completed, often after a delay of weeks or months, providing stale information. Such traditional surveys use standard sets of questions that cannot gather information with insight into the reasons for the responses. Desirable are automated survey programs that capture the logic a skilled questioner (for example, a process consultant or a physician) uses to glean knowledge about a process or a patient.

It would also be desirable to have better surveying techniques utilizing data from different sources (such as patient information about physician office process, employee satisfaction data, and practice fiscal performance data) which are combined as the data are collected, analyzed immediately, with that information being presented across the internet in real time once collected, and immediately available.

It would be further desirable if survey information were made ready for presentation using an information rich graphical display method. One such method, using a particular clinical improvement process, is the subject of a co-pending application titled "Method And System For Presentation Of Survey And Report Data", Ser. No. 19/911,915, incorporated herein by reference, which uses a clinical improvement process utilizing a "compass" viewpoint presentation format (described therein, and hereinbelow). Using such a graphical display format, the information can be presented so that the end user gets a balanced scorecard presentation of the things that can affect the physician office environment.

Survey capabilities that would prove useful to service providers in general, and more specifically, medical care providers, are those that collect data from individuals about the service, e.g., the health care delivery experience, providing nearly instantaneous reports that include, for example, information: 1) from patients about their experience while visiting physician offices; 2) from patients about their ability to do activities of everyday life ("Functional Health Status"); 3) from patients about their age, gender, and condition specific health needs; and 4) from physician office employees about their experience of work, and from the office manager about the efficiency of the health care office.

The Integrated Communication System [ICS], described in application Ser. No. 09/871,279 and incorporated herein by reference, provides a tool that can be used to automate the survey process to reduce the number of human beings utilized in the survey process, to increase the accuracy, reduce the costs, improve the efficiencies, and overcome the shortcomings of current techniques identified above.

The ICS utilizes modern computer and networking technology, along with advances in automated voice recognition, database design, computer processing, and computer networking, all to provide means to improve the process of performing a survey. Accordingly, the ICS can provide a platform to overcome some of the shortcomings of traditional means of evaluating the quality of services of a health care provider (such as physician offices) that were identified above. The Integrated Communication System (ICS) can be used in a similar manner that a database programmer would use a commercially available software development environment to build a commercially available computer software program.

Using the ICS programming environment, survey programs can be developed to collect relevant data from respondents in real-time to exclude or include large amounts of query material specifically relevant to the particular individual being queried. Only questions relevant to the specific respondent are asked, and large bodies of information are avoided. Data from respondents is analyzed, compared to normative population data, and presented graphically to the respondent and other users of the program for action.

The POVS uses the ICS environment to capture the logic of a skilled questioner (a physician, a process consultant) by codifying subject mater knowledge and logic in a series of immediately executable commands that allow the computer to ask a series of logically connected and interdependent questions. The sequence and scope of the questions parallels that of a skilled observer of physician office function and/or of a physician asking questions about a person's health. The invention also processes the collected information to provide the health care provider with useful quality information using the compass viewpoint paradigm, providing the health care provider with tools and information to assess the quality of his organization's product(s) and/or service(s).

SUMMARY OF THE INVENTION

The Physician Office Viewpoint Survey System and Method [POVS] is a system for collecting, processing, and presenting survey information to medical care providers for quality control programs and process improvements. The POVS utilizes the Compass viewpoint information presentation paradigm.

The POVS includes an automated survey communication system which connects a survey participant to the POVS. The automated survey system obtains participant survey data by executing software scripts provided by POVS programs.

The POVS also includes a patient viewpoint module for providing software scripts to the survey communication system for surveying survey participants who are patients. The patient viewpoint module also receives the survey data, including patient survey data, obtained from the patient from the survey communication system.

The POVS has a personal clinical data analysis module for generating analyzed data generated by analyzing the collected survey data. Further, the personal clinical data analysis module generates reports on the analyzed data for use by a survey consumer;

The POVS also has an office team viewpoint module which provides software scripts to the survey communication system for surveying survey participants who are employees, contractors, or other workers, to obtain employee survey data.

Also included is an office fiscal performance viewpoint module which provides software scripts to the survey communication system for surveying survey participants who are managers, and further which receives survey data, including fiscal performance data, obtained from the manager.

Finally, the POVS includes a physician office data presentation module for generating assessed and analyzed survey information for presenting to end users in a formatted manner.

The POVS utilizes various databases to store and retrieve both the collected, analyzed, and historical data for comparison purposes for display to the POVS user (consumer).

The POVS utilizes the following survey process steps:
  connecting to a survey participant over an external communication system;
  conducting a plurality of automated surveys with survey participants, said automated surveys being conducted according to survey scripts providing instructions for conducting the automated survey to collect survey data. The automated surveys include:
    conducting a survey with a participant who is a patient according to patient survey scripts, including scripts for obtaining patient viewpoint data;
    conducting a survey with a participant who is an employee according to employee survey scripts including scripts for obtaining employee viewpoint data; and
    conducting a survey with a participant who is a manager according to manager survey scripts including scripts for obtaining fiscal performance data;
  generating analyzed data from the collected survey data, wherein the analyzed data utilizes the clinical compass viewpoint paradigm;
  generating reports for use by a survey consumer and/or a survey participant, the reports utilizing both the survey data and the analyzed data; and
  generating formatted survey information from the survey data and the analyzed data for display to a survey consumer.

BRIEF DESCRIPTION OF THE DRAWINGS

FIG. 9 is a first part of a Health Action Form output of one embodiment of the invention.

FIGS. 10A and 10B, in combination, show a second part of the Health Action Form of FIG. 9.

DETAILED DESCRIPTION OF THE INVENTION

The Physician Office Viewpoint Survey [POVS] System and Method provides an automated, computerized means for evaluating the quality of service providers in general, and medical service providers, especially doctor offices, in particular. The POVS is described as it would be implemented in a medical care service provider setting, such as for a physicians office. However, the techniques and methods disclosed herein are applicable to any industry where good customer service and quality improvement are considered important objectives.

The POVS allows data to be quickly obtained by surveying service customers, and then rapidly analyzed and processed for display and evaluation. A process that has taken weeks and even months using traditional surveying techniques can be reduced to days or even hours. Most of the time is spent collecting the data from users in an automated, computerized fashion, while actual analysis and production of the results is nearly instantaneous once a sufficient number of users have been surveyed to provide meaningful results. Consumers of the survey information can see the results of the surveys being updated regularly. Update frequency is limited only to the resources provided for collecting the survey data (which can be automated), or the number of available survey participants.

Figure 1:
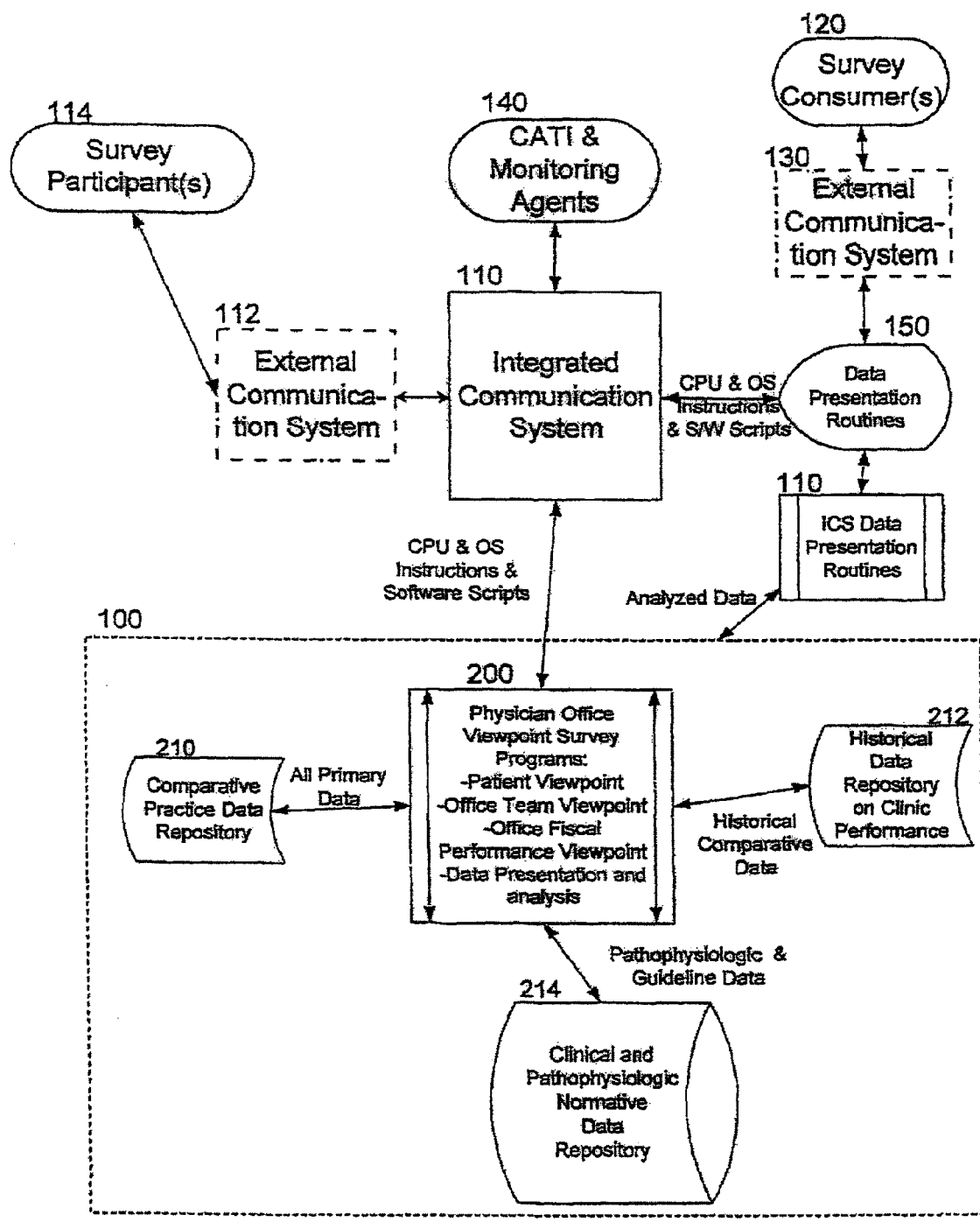
FIG. 1 is a block diagram showing the Physician Office Viewpoint Survey System in the context of its operating environment with major components.

FIG. 1 shows a diagram of the Physician Office Viewpoint Survey System [POVS] 100 and its relationship between the Integrated Communication System [ICS] 110, and survey participants/respondents 114 and medical survey consumers 120. The POVS System uses the ICS 110 programming environment and operating system to execute its logic.

Survey participants 114 (also called survey respondents) include consumers of the medical services provided by the medical provider. Survey participants might also include employees and contractors of the medical provider. Survey participants interact with the POVS 100 via an External Communication System [ECS] 112 using the ICS 110 in one embodiment.

Survey consumers 120 include the medical care provider representatives, especially management, doctors, and other senior personnel, as well as other employees or contractors participating in quality improvement. Survey consumers 120 interact with the POVS 100 via an External Communication System [ECS] 130. The ECS 130 may be different, or the same, as the ECS 112.

The ECS 112 and/or the ECS 130 might include, for example, a telephone, Internet telephony, a radio network, private networks, World Wide Web servers and clients, among other possible communication devices. Standard communication protocols would be utilized, as long as those protocols meet the needs of the POVS 100. Otherwise, a custom protocol could be developed. The ICS 110 (described in more detail in the co-pending Integrated Communication System and Method, application Ser. No. 09/871,420, incorporated herein by reference) interacts with the survey participants 114 via the ECS 112, obtaining detailed survey data for input into the POVS 100. However, the POVS 100 is not restricted to utilizing the ICS 110 environment for performing the customer surveying activity, as other surveying methods and systems can be utilized to populate the POVS 100 databases.

The POVS 100 utilizes the ICS 110, or some other surveying methodology and execution platform, for interacting with survey participants 114 to obtain survey data. Methods of surveying medical care consumers useful for applying to the POVS are discussed in the Interactive Survey And Data Management Method, application Ser. No. 09/871,279, incorporated herein by reference. The POVS 100 utilizes the ICS 110, or some other execution platform, to execute the algorithms and host the databases useful for implementing the POVS. The various software modules of the POVS 100 provide scripts to the ICS 110 to be executed and implemented into an automated survey. These scripts, described in more detail hereinbelow, are used to define the specific survey structure, questions, scope, logic, and timing, and presentation format that the ICS 110 will use to perform the survey with a particular participant 114.

Figure 2:
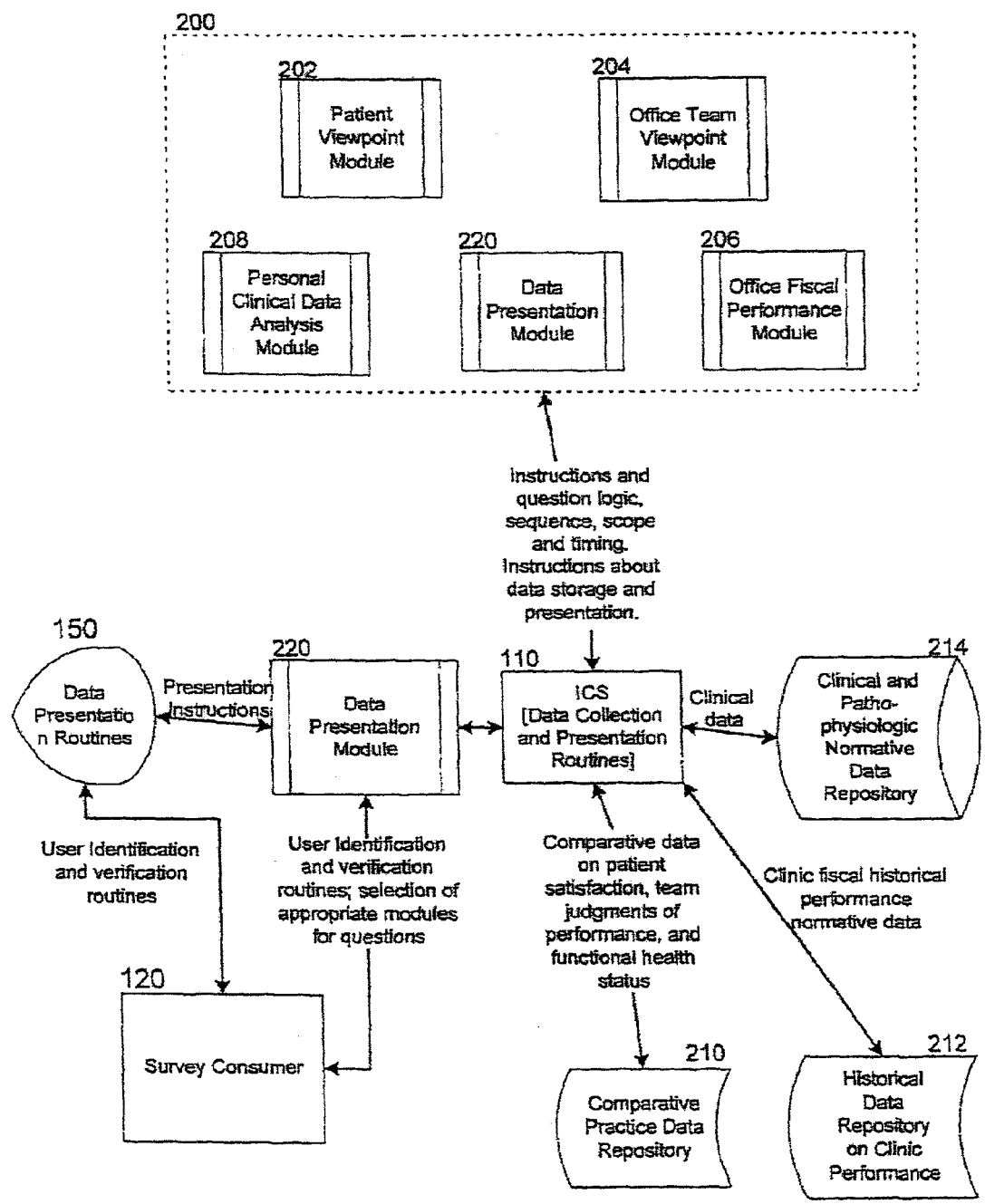
FIG. 2 is a block diagram showing the Physician Office Viewpoint Survey System exploded into its top-level components in a preferred embodiment, with major data flows between them identified.

FIG. 2 shows an exploded block diagram of an embodiment of the POVS system, showing four software modules, three data repositories, and the relationships between them.

The Physician Office Viewpoint Survey Subsystem 200 utilizes four modules to collect data: A Patient Viewpoint Module 202, an Office Team Viewpoint module 204, an Office Fiscal Performance Viewpoint Module 206, a Personal Clinical Data Analysis Module 208, and a Physician Office Data Presentation Module 220.

The Physician Office Viewpoint Survey Subsystem 200 stores and retrieve data from three databases: the Comparative Practice Data Repository 210, the Historical Data Repository on Clinical Performance 212, and the Clinical and Pathophysiologic Normative Data Repository 214.

The Comparative Practice Data Repository 210 stores data collected from the surveys with participants; i.e. the responses to the questions collected from survey respondents in the various surveys that run on the Physician Office Viewpoint Survey Programs 200. It is stored for use by the survey participant 114 and the POVS in general, and this repository 210 also allows comparison across the universe of respondents for use by the survey consumer 120. This data can be used for cohort comparisons. It is a primary source database.

The Historical Data Repository on Clinic Performance 212 is a database that contains historical performance data on key metrics that can be used to predict clinic fiscal success. This data is derived from public and private (purchased) data that has been synthesized, combined, reworked, analyzed and formatted for use by the POVS. It is a primary and secondary source database.

The Clinical and Pathophysiologic Normative Data Repository 214 contains data obtained from various sources that relates to age, gender, and specific conditions of patients. For example, it could contain the national, publicly accepted guidelines on cholesterol screening, among others. This database could also contain all the age- and gender-relevant preventative health, and the age- and gender-relevant screening guidelines from the US Preventative Services Task Force Guidelines report to the US Department of Health and Human Services. In addition, this database could also house derived data from the medical literature and treatises about the leading causes of death and morbidity by age and gender. It could also contain proprietary literature about the US Preventative Services Task Force Guidelines Summary Recommendations. The literature is written for respondents and clinicians so that, if the respondent has behaviors or risk factors that are outside what is accepted as "normal," the respondent can follow the guidelines with instructions from the literature database and bring them into compliance with the guideline recommendations. The database also contains normative data about age- and gender-relevant pathophysiologic states.

The Physician Office Viewpoint Survey Subsystem 200 can utilize Data Presentation Routines and Visual Display features of the ICS 110 and its included clinical improvement process and compass viewpoint paradigm, to present data in a unique graphical format to survey consumers.

The Physician Office Viewpoint Survey Subsystem 200 collects survey data reported by survey participants/respondents 114 in real-time or near real-time over an ECS 112 using, in one embodiment, the ICS 110. The data are analyzed and compared against relevant normative or cohort data, and stored for immediate or future use in analysis and presentation. The programs use an internally consistent logic to select questions for presentation. For example, a 72-year-old respondent will answer some different questions than a 24-year-old respondent based upon age, gender, and medical condition. As another example, a person delighted with a clinic's front desk performance may be asked some different questions than a person who has had a bad experience with the front desk. Accordingly, the POVS tailors the survey questioning according to the specific responses or variables associated with a particular participant 114.

The ICS 112 Data Presentation Routines and Physician Office Viewpoint Survey Subsystem 200 are robust in their ability to analyze and present data in real-time or near real-time. An end user (such as the survey consumer 120) can specify any of the survey questions and designate it as a dependent or independent variable, design data display, and present the data in a matter of seconds. The presentation data may or may not include data obtained from the data repository(s) at the users discretion.

The POVS 100 typically interacts with the respondent(s)/participant(s) 114 via the ECS 112 and the ICS 110 to collect survey data. A POVS module will provide a specific script program for execution by the ICS 110 based upon the preferences of the end user. This script has instructions on the skip logic and tells which command(s) the ICS 110 should perform next. The ICS 110, or some other surveying platform, executes the command(s) provided by the script. The ICS 110 then provides inputs to the appropriate database according to the script. In other words, the ICS 100 provides an operating environment for the programs and scripts, which are comprised of instruction sets written for that ICS 110 environment. The scripts and programs included in the Physician Office Viewpoint Survey Subsystem 200 modules provide the logic (questions, sequence, timing, and scope) for the ICS 110, directing the ICS 110 devices to execute the script's directives and display outputs according to a logic, sequence, timing, and scope that are specified in the script/program. The script/program also calls static data (text, for example) from databases that are historical or factual (as opposed to dynamic and primary source databases).

The data collection survey performed by the ICS 110, according to the scripts and programs of the various Physician Office Viewpoint Survey Subsystem 200 modules can have both fixed and variable questions. The fixed questions represent core domains that every respondent is asked to complete about the respondent's experience with the physician office visit. Core domains match the main office processes that a patient experiences in the course of care, and are asked of every respondent because every respondent experiences these processes as they pas through the physician office. In addition, The Physician Office Survey queries the respondent in a variable fashion within each core domain. Variable questions are not asked of every respondent, rather questions are presented to each respondent based upon the respondent's last responses, and/or based on particular information about the respondent. The computer uses its programming logic to select the most relevant variable questions to present to the respondent. In this manner, the respondent is asked the most relevant information in a time efficient manner. The respondent does not answer questions that are not relevant to his experience. Accordingly, the data collected in this manner is extremely efficient and tailored specifically to the experience of the respondent.

Figure 3:
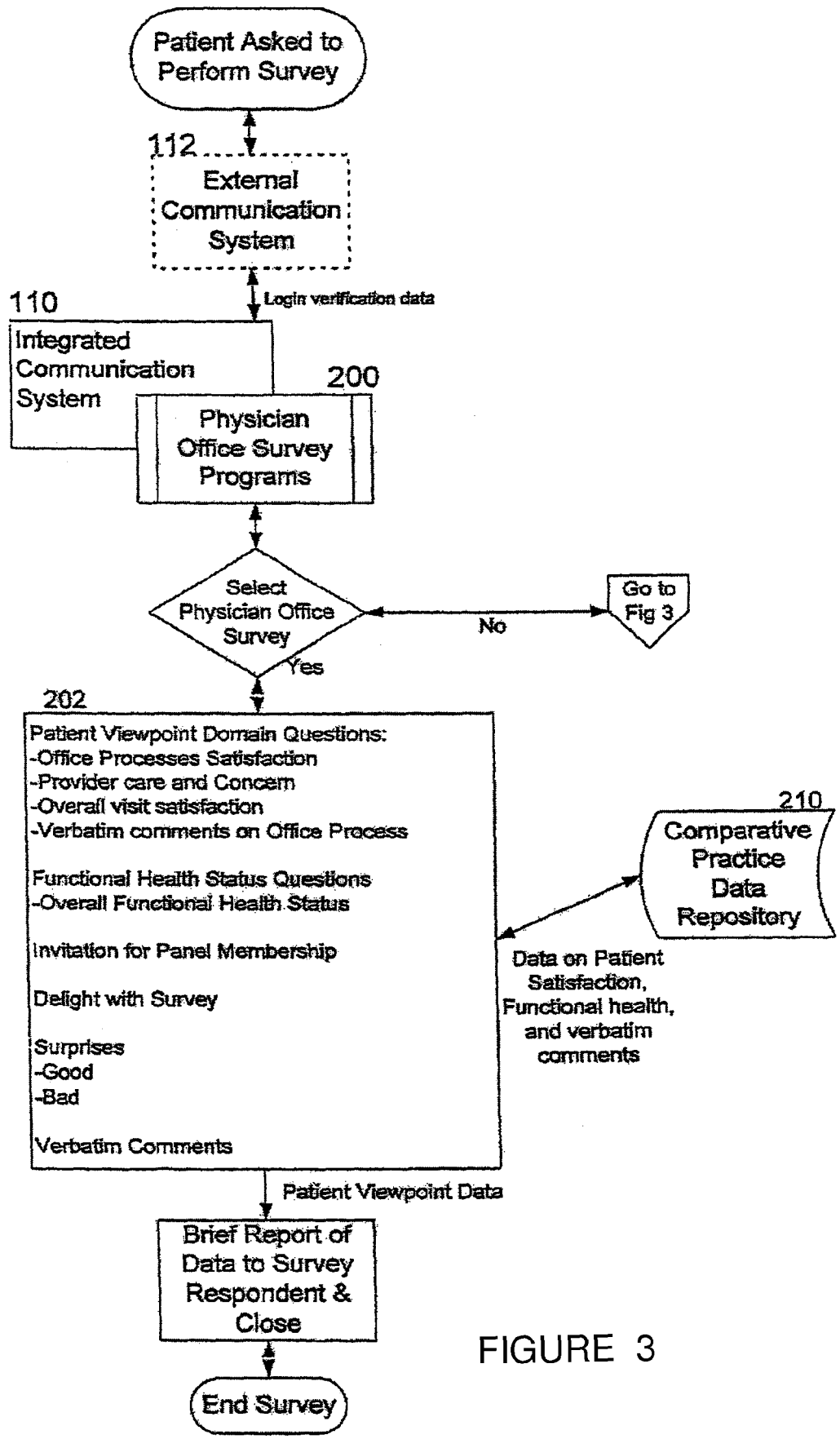
FIG. 3 is a block diagram showing an example of the major functionality and interfaces of the Patient Viewpoint Module.

FIG. 3 describes the operation of the Patient Viewpoint Module 202 of the Physician Office Survey Subsystem 200. A respondent is connected to the ICS 110 through the ECS 112 (such as the Internet, for example), which provides respondent access to the ICS 110. The Physician Office Survey Subsystem 200 verifies that the respondent, in this case a present or former patient, is an appropriate and valid user, and activates the Physician Office Survey programs for use. The Patient Viewpoint Module 202 provides the ICS 110 with the scripts to interact with the participant 114 (e.g., a patient) and thus perform the desired survey or survey subset.

Core domain questions as part of the survey implemented by the Patient Viewpoint Module 202 on the ICS 110 represent overall process satisfaction, provider care and concern, and overall visit satisfaction. Verbatim comments may be collected on the office process. In addition, the Patient Viewpoint Survey Module 202 directs the ICS 110 to collect information on respondent's (e.g., a patient's) functional health status.

Patient respondents also can be invited to become survey panel members. If a respondent chooses to be a panel member, then the respondent is queried on a periodic basis about the experiences at the provider office, providing regular updates as to the performance of the medical care provider.

Patient respondents are asked to comment on any good or bad surprises they experienced in their office visit, and record any other verbatim comments that they might want to share with the physician's office.

If some cases, the Patient Viewpoint Module 202 will present a brief report of the respondent's results back to the patient (via the ICS 110 over the ECS 112) before closing. This allows the respondent to know how their responses compare to a similar cohort of respondents.

Data checking is performed by the Module 202, and occurs at the time of data collection—the program for storage does not accept data that is incompatible with the database. Data are stored in the Comparative Practice Data Repository 210 and compared by the Module 202 to the Historical Data Repository 212 on Clinic Performance. It is possible to store and analyze the responses from millions of respondents. Data are analyzed by Module 202 for content items, data integrity, and completeness. Data are analyzed by the Module 202 program at storage and when called for display.

Responses to the Patient Viewpoint Survey Module 202 are stored in real-time or near real-time in the Comparative Practice Data Repository 210 and are immediately available for use by Data Presentation Routines of the ICS 110 for data analysis and presentation to the end user. This allows virtually instant use of survey results by a survey consumer 120. Moreover, the survey data can be analyzed by the POVS 100 analysis modules in a limitless number of ways immediately at the discretion of the survey consumer 120. The survey responses can be compared to cohort or national comparative groups, presented by the POVS.

Examples of high-level software scripts used by the Patient Viewpoint Module 202 are given below, but they are for illustration purposes only, as the actual scripts utilized in any particular implementation depend on the specific objectives to be achieved for that implementation:

Physician Office Compass viewpoint—Patient Viewpoint
PtIntroduction
Signpost: Welcome!
Read(NI): Thank you for taking part in this Quality Data Management survey. Your health care provider's office has asked us to conduct this survey for them.
Read(I): |The term "health care provider" refers to the person you saw during your visit. A health care provider can be a doctor, nurse practitioner, physician assistant, or nurse midwife.
Read(I): |The results of the survey will be used to make improvements in the care that patients receive. The survey takes about 5 minutest to complete, and your answers will remain strictly confidential.
Read(N): The results of the survey will be used to make improvements in the care that patients receive.
Note: PD: Is a bar (|) needed in the last script item, which is Net only (before the Read(N))?
Note: This definition of "health care provider" is based in part on the CAHPS 2.0H Adult Commercial survey, item 16.
Speech: In0042E; In0042F; In0042G
Voice: (SilenceRepeat) I did not quite hear you. Would you please say that again?
Voice: (GarbledRepeat) Would you repeat that again?
Voice: (VoiceFileMissing) We experienced a temporary system problem. Please continue to the best of your ability.
PtIntroIVR
Read(I): The questions for this survey have been pre-recorded, and you give your answers by speaking directly into your phone. You don't have to push any buttons; simply wait until you hear all the response choices, choose one, and then say that answer out loud.
Read(I): |Please reserve any comments until the end of the survey, where you are asked to give your comments in your own words.
Read(I): |If at anytime during this survey, you want a question to be repeated, just say, "Please Repeat."
Speech: In0043A; In0043B; In0043C
PtConfirm
Signpost: Confirming Your Visit
Read(NI): First, I need to confirm that you recently visited your health provider's office. Is this correct?
Read(I): |Please say 'Yes' or 'No.'
<1> Yes {goto PtAccessCode}
<2> No {goto PtNoSurvey}
Source: POCp
Vocabulary: yesno2

Handling: High
Speech: In0139C; Ix1199 (SilenceRepeat, Ix1199)
PtNoSurvey
Signpost: Thank You
Read(NI): Thank you for your time, but for the purpose of this study, we are only conducting this survey with people who recently visited a health care provider's office. Goodbye.
{done}
Source: POCp
Speech: C9019A
PtAccessCode
Signpost: Confirming Your Visit
Read(N): Please type the access code printed on the card that you received from the office.
Read(I): Please say the access code printed on the card that you received from the office.
<text>
Source: POCt
Speech: In0140A (SilenceRepeat, GarbledRepeat)
Handling: Low (Thoughtful)
PtProviderName
Read(I): Please say the name of the provider that you saw during this visit.
<text>
Read(N): Please choose the name of your Clinic {lookup ClinicTable ClinicTableNames ClinicNames}
Read(N): Please choose the name of your provider {lookup ProviderTable ProviderTableNames ProviderNames}
Source: POCp
Speech: In0155
Handling: Low (Thoughtful)
PtRepeatReminder
Read(I): Thank you. Before we begin, I want to remind you that you can hear a question again at anytime during the survey; all you have to do is say, "Please repeat."
Speech: In0045
PatientLeadIn
Signpost: Your Recent Visit
Read(N): Let's begin! The following questions are about your recent visit to a health care provider's office.
Read(I): And now let's begin! The following questions are about your recent visit to a health care provider's office. Please answer each of the following questions by saying, "Excellent, Very good, Good, Fair, Poor, or Does not apply."
Source: POCsfp
Speech: L1727
PtQ1
Signpost: Getting An Appointment For This Visit
Read(NI): How would you rate getting through to the office by phone?
Read(I): |'Excellent,' 'Very good,' 'Good,' 'Fair,' 'Poor,' or 'Does not apply'? Voice: (Ix1161a) Please say 'Excellent,' 'Very good,' 'Good,' 'Fair,' 'Poor,' or 'Does not apply.'
<1> Excellent
<2> Very good
<3> Good
<4> Fair
<5> Poor
<6> Does not apply
<8> DON'T KNOW OR REFUSAL
Vocabulary: EpDna
Handling: Medium (Normal)
Speech: Qac3018; Ix1161 (SilenceRepeat, Ix1161a)
ShortName: Getting Thru by Phone
LongName: Rating of Getting Through to Office by Phone
Structure: Patient Satisfaction; Initiating Care
ValidRange: 5, 1
ValueLabels: Ep5
PtQ2
Read(NI): How would you rate how long you waited to get an appointment?
Read(I): |'Excellent,' 'Very good,' 'Good,' 'Fair,' 'Poor,' or 'Does not apply'?
Voice: (Ix1161a) Please say 'Excellent,' 'Very good,' 'Good,' 'Fair,' 'Poor,' or 'Does not apply.'
<1> Excellent
<2> Very good
<3> Good
<4> Fair
<5> Poor
<6> Does not apply
<8> DON'T KNOW OR REFUSAL
Vocabulary: EpDna
Handling: Medium (Normal)
Speech: Qac3016; Ix1161 (SilenceRepeat, Ix1161a)
ShortName: Wait For Appointment
LongName: Rating of Wait for Appointment
Structure: Patient Satisfaction; Initiating Care
ValidRange: 5, 1
ValueLabels: Ep5
PtQ3
Signpost: At This Visit
Read(NI): How would you rate the length of time spent waiting at the office?
Voice: (Ix1161a) Please say 'Excellent,' 'Very good,' 'Good,' 'Fair,' 'Poor,' or 'Does not apply.'
Note: PD: At this point in IVR, we stop giving the response choices unless there is silence or garbled. If silence, give the response instruction & then repeat the question. If garbled, just give the response instruction.
<1> Excellent
<2> Very good
<3> Good
<4> Fair
<5> Poor
<6> Does not apply
<8> DON'T KNOW OR REFUSAL
Vocabulary: EpDna
Handling: Medium (Normal)
Speech: Qac3019 (Ix1161a;Qac3019, Ix1161a)
ShortName: Office Wait
LongName: Rating of Time Spent Waiting at Office
Structure: Patient Satisfaction; Initiating Care
ValidRange: 5, 1
ValueLabels: Ep5
PtQ4
Read(NI): How would you rate the sensitivity of all the staff to your special needs or concerns?
Voice: (Ix1161a) Please say 'Excellent,' 'Very good,' 'Good,' 'Fair,' 'Poor,' or 'Does not apply.'
<1> Excellent
<2> Very good
<3> Good
<4> Fair
<5> Poor
<6> Does not apply
<8> DON'T KNOW OR REFUSAL
Vocabulary: EpDna
Handling: Medium (Normal)
Speech: Qac3061 (Ix1161a; Qac3061, Ix1161a)
ShortName: Sensitivity to Needs LongName: Rating of Sensitivity to Special Needs or Concerns
Structure: Patient Satisfaction; Receiving Care
ValidRange: 5, 1
ValueLabels: Ep5
PtQ5
Signpost: Provider's Care At This Visit
Read(NI): How would you rate the provider's caring and concern?
Voice: (Ix1161a) Please say 'Excellent,' 'Very good,' 'Good,' 'Fair,' 'Poor,' or 'Does not apply.'
<1> Excellent
<2> Very good
<3> Good
<4> Fair
<5> Poor
<6> Does not apply
<8> DON'T KNOW OR REFUSAL
Vocabulary: EpDna
Handling: Medium (Normal)
Speech: Qac3064 (Ix1161a; Qac3064, Ix1161a)
ShortName: Provider's Caring
LongName: Rating of Provider's Caring & Concern
Structure: Patient Satisfaction; Provider's Care
ValidRange: 5, 1
ValueLabels: Ep5
PtQ6
Read(NI): How would you rate how well the provider explained things to you?
Read(I): |Please say, 'Excellent,' 'Very good,' 'Good,' 'Fair,' 'Poor,' 'Provider didn't explain things,' or 'Does not apply'?
<1> Excellent
<2> Very good
<3> Good
<4> Fair
<5> Poor
<6> Provider didn't explain things
<7> Does not apply
<8> DON'T KNOW OR REFUSAL
Vocabulary: EpDna6
Handling: Medium (Normal)
Speech: Qac3063; Ix1161d (SilenceRepeat, Ix1161d)
ShortName: Provider Explanation
LongName: Rating of Provider's Explanations
Structure: Patient Satisfaction; Provider's Care
ValidRange: 6, 1
ValueLabels: Ep6 Explained
PtQ7
Read(NI): How would you rate the provider's thoroughness, carefulness, and technical skill?
Voice: (Ix1161a) Please say 'Excellent,' 'Very good,' 'Good,' 'Fair,' 'Poor,' or 'Does not apply.'
1> Excellent
<2> Very good
<3> Good
<4> Fair
<5> Poor
<6> Does not apply
<8> DON'T KNOW OR REFUSAL
Vocabulary: EpDna
Handling: Medium (Normal)
Speech: Qac3065 (Ix1161a; Qac3065, Ix1161a)
ShortName: Provider's Skill
LongName: Rating of Provider's Thoroughness, Carefulness, Technical Skill
Structure: Patient Satisfaction; Provider's Care
ValidRange: 5, 1
ValueLabels: Ep5
PtQ8
Read(NI): How would you rate the amount of time your provider spent with you?
Voice: (Ix1161a) Please say 'Excellent,' 'Very good,' 'Good,' 'Fair,' 'Poor,' or 'Does not apply.'
1> Excellent
<2> Very good
<3> Good
<4> Fair
<5> Poor
<6> Does not apply
<8> DON'T KNOW OR REFUSAL
Vocabulary: EpDna
Handling: Medium (Normal)
Speech: Qac3062 (Ix1161a; Qac3062, Ix1161a)
ShortName: Amt Time w/Provider
LongName: Rating of Amount of Time Spent with Provider
Structure: Patient Satisfaction; Provider's Care
ValidRange: 5, 1
ValueLabels: Ep5
PtQ9
Signpost: Other Aspects Of Care At This Visit
Read(NI): How would you rate the degree to which you were involved in making decisions about your care?
Voice: (Ix1161a) Please say 'Excellent,' 'Very good,' 'Good,' 'Fair,' 'Poor,' or 'Does not apply.'
<1> Excellent
<2> Very good
<3> Good
<4> Fair
<5> Poor
<6> Does not apply
<8> DON'T KNOW OR REFUSAL
Vocabulary: EpDna
Handling: Medium (Normal)
Speech: Qac3066 (Ix1161a; Qac3066, Ix1161a)
ShortName: Involve in Decisions
LongName: Rating of Involvement in Making Decisions
Structure: Patient Satisfaction; Receiving Care
ValidRange: 5, 1
ValueLabels: Ep5
PtQ10
Signpost: The Visit Overall
Read(NI): How would you rate the outcome of your visit—that is, how much it helped you?
Voice: (Ix1161a) Please say 'Excellent,' 'Very good,' 'Good,' 'Fair,' 'Poor,' or 'Does not apply.'
<1> Excellent
<2> Very good
<3> Good
<4> Fair
<5> Poor
<6> Does not apply
<8> DON'T KNOW OR REFUSAL
Vocabulary: EpDna
Handling: Medium (Normal)
Speech: Qac3067 (Ix1161a; Qac3067, Ix1161a)
ShortName: Outcome
LongName: Rating of Outcome of Visit
Structure: Patient Satisfaction; Overall ValidRange: 5, 1
ValueLabels: Ep5
PtQ11
Read(NI): And, how would you rate the overall quality of care and services you received?
Voice: (Ix1161a) Please say 'Excellent,' 'Very good,' 'Good,' 'Fair,' 'Poor,' or 'Does not apply.'
<1> Excellent
<2> Very good
<3> Good
<4> Fair
<5> Poor
<6> Does not apply
<8> DON'T KNOW OR REFUSAL
Vocabulary: EpDna
Handling: Medium (Normal)
Speech: Qac3068 (Ix1161a; Qac3068, Ix1161a)
ShortName: Overall Quality
LongName: Rating of Overall Quality of Care & Services
Structure: Patient Satisfaction; Overall
ValidRange: 5, 1
ValueLabels: Ep5
PtYesNo
Signpost: About This Visit in General
Read(NI): Here are a few more questions about your most recent visit to this provider's office.
Speech: L1728
PtQ12
Read(NI): Was your appointment scheduled with the provider you wanted to see?
Read(I): |Please say, 'Yes,' 'No,' or 'Does not apply, I did not specify a provider.'
<1> Yes
<2> No
<3> Does not apply; I did not specify a provider
<8> DON'T KNOW OR REFUSAL
Vocabulary: YNDna
Speech: Qac3069; Ix1199np (SilenceRepeat, Ix1199np)
ShortName: Saw Provider Wanted
LongName: Whether Saw Provider Wanted to See
Structure: Patient Satisfaction; Receiving Care
ValidRange: 2, 1
ValueLabels: Ynp
PtQ13
Read(NI): Were there any problems having a chance to ask all of your questions?
Read(I): |Please say, 'Yes,' 'No,' or 'Does not apply.'
<1> Yes
<2> No
<3> Does not apply
<8> DON'T KNOW OR REFUSAL
Vocabulary: YNDna
Speech: Qac3070; Ix1199na (SilenceRepeat, Ix1199na)
ShortName: Cannot Ask Questions
LongName: Whether Problems Having Chance to Ask Questions
Structure: Patient Satisfaction; Receiving Care
ValidRange: 1, 2
ValueLabels: YN
PtQ14
Signpost: Tell Us In Your Own Words
Read(NI): Next is a question without any response choices. We would like you to answer the question in your own words. Here is the question,
Read(NI): |What could the provider's office do to improve care and better meet your needs?
Voice: (V3071C) Please say in your own words, what could the provider's office do to improve care and better meet your needs?
<text>
Handling: Low (Thoughtful)
Speech: V3071A;V3071B (V3071C)
ShortName: What Could Improve
LongName: What Provider's Office Could Do To Improve Care
Structure: Patient Satisfaction; Verbatims
PtAboutYou
Signpost: About You
Read(NI): Next are 3 important questions about you.
Speech: L1729
PtQ15
Read(NI): In general, how would you rate your overall health now? Is it . . . .
Read(I): |'Excellent,' 'Very good,' 'Good,' 'Fair,' or 'Poor'?
Voice: (Ix1160a) Please say 'Excellent,' 'Very good,' 'Good,' 'Fair,' or 'Poor.'
<1> Excellent
<2> Very good
<3> Good
<4> Fair
<5> Poor
<8> DON'T KNOW OR REFUSAL
Vocabulary: Ep
Handling: Medium (Normal)
Speech: Qac3072; Ix1160 (SilenceRepeat, Ix1160a)
ShortName: General Health
LongName: Rating of Overall Health Now
Structure: Patient Satisfaction; Personal Functioning
ValidRange: 5, 1
ValueLabels: Ep5
PtQ16
Read(NI): What age group are you in?
Read(I): |'24 years or under,' '25 to 34 years,' '35 to 44 years,' '45 to 64 years,' or '65 years or over'?
<1> 24 years or under
<2> 25 to 34 years
<3> 35 to 44 years
<4> 45 to 64 years
<5> 65 years or over
<8> DON'T KNOW OR REFUSAL
Vocabulary AgeGrp
Handling: Low (Normal)
Speech: D8125; Ix1263
ShortName: Age Group
LongName: Age Group
Structure: Patient Satisfaction; Personal Demographics
ValidRange: 1, 5
ValueLabels: AgeGroup
PtQ17
Read(NI): Are you male or female?
<1> Male
<2> Female
<8> DON'T KNOW OR REFUSAL
{if PanelEligible=0 then goto PtThisSurvey}
Vocabulary: gender
Handling: Low (Normal)
Speech: D8126 (D8126)
ShortName: Gender
LongName: Gender
Structure: Patient Satisfaction; Personal Demographics
ValidRange: 1, 2
ValueLabels: Gender PtPanelInvite
Signpost: The Advisory Group
Read(NI): Thank you for doing this confidential survey. Your doctors especially need your feedback to make their practice as good as it can possibly be. Some patients are being chosen to be part of a special advisory group. This group includes patients who will periodically complete surveys that are similar to this one.
Read(N): If you choose to join the group, Quality Data Management will ask for your e-mail address. We would send you an e-mail message every 2 or 3 months to find out if you visited the medical practice during this time. If so, we would direct you to our web site to complete another survey.
Read(I): If you choose to join the group, Quality Data Management will ask for your telephone number. We would call you every 2 or 3 months to find out if you visited the medical practice during this time. If so, we would direct you to call our toll-free number to complete another survey.
Read(NI): |Would you be interested in joining the advisor group?
Voice: (Ix1199) Please say, 'yes' or 'no.'
<1> Yes
<2> No
<8> DON'T KNOW OR REFUSAL
{if PtPanelInvite=2 then goto PtThisSurvey}
Source: POCsfp
Vocabulary: yesno2
Handling: High
Speech: Qac3073A; Qac3073B; Qac3073C (SilenceRepeat, Ix1199; Qac3073C)
PtEMailPhone
Read(N): What is your e-mail address? This information will be held in strictest confidence by Quality Data Management and will be used only for the purpose of helping to receive your anonymous feedback.
Read(I): What is your telephone number, including your area code? This information will be held in strictest confidence by Quality Data Management and will be used only for the purpose of helping to receive your anonymous feedback.
Voice: (Qac3074A) Please say your phone number, including your area code.
<text>
Handling: Low (Thoughtful)
Speech: Qac3074 (SilenceRepeat, Qac3074A)
PtThisSurvey
Signpost: About This Survey
Read(N): This completes the survey. Before you go, I have two questions about the survey itself. Were you satisfied with the way this survey was conducted?
Read(I): This completes the survey. Before you go, I have one more question about the survey itself Were you satisfied with the way this survey was conducted?
Voice: (Ix1199) Please say, 'yes' or 'no'.
<1> Yes
<2> No
<8> DON'T KNOW OR REFUSAL
{If IVR=1 then goto PtClosing}
Vocabulary: yesno2
Speech: C9005D (SilenceRepeat, Ix1199)
PtDelightDissappt
Read(N): Please tell us what you thought about this interview process. We are especially interested in learning about anything you liked or disliked.
Note: PD: DHH: This item should be skipped in IVR. Do we need an instruction in the preceding item to make it do that?
<text>
Speech: C9006B (C9006B)
Handling: Low (Thoughtful)
PtClosing
Signpost: Thank You!
Read(NI): Thank you very much for participating in this survey. Goodbye.
{done}

Figure 4:
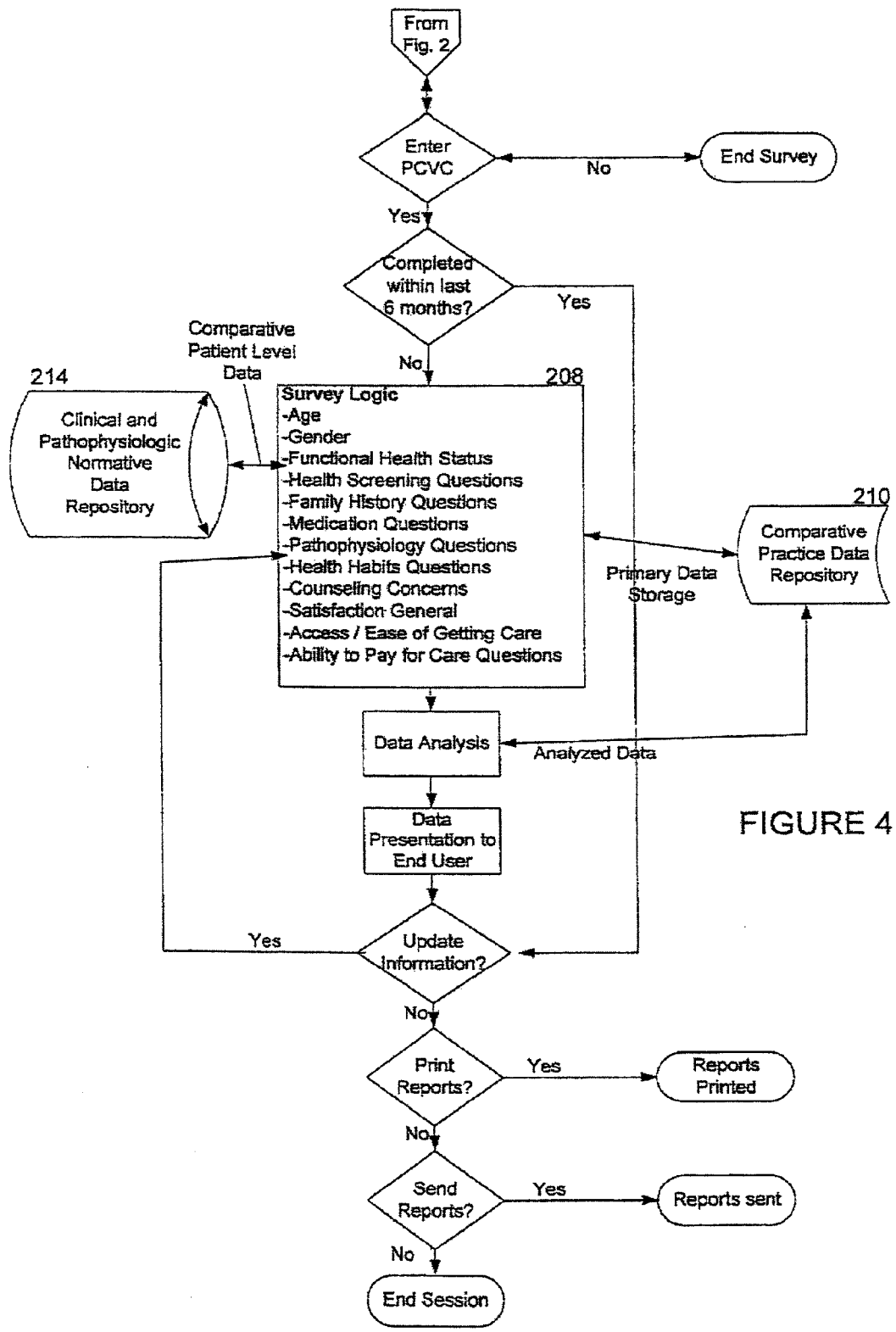
FIG. 4 is a block diagram showing an example of the major functionality and interfaces of the Personal Clinical Data Analysis Module.

FIG. 4 shows the operation of the Personal Clinical Data analysis module 208. Respondents 114 activate the Personal Clinical Data analysis module 208 programs via the ICS 110 through an external communication system 112.

If the respondent 114 is a new user or has not updated the information within a certain period of time, six months in one embodiment, the respondent may be asked age, gender, and condition specific questions by the Personal Clinical Data analysis module 208 in order to keep this information current.

The Personal Clinical Data analysis module 208 implements a survey logic, selecting specific questions to present to the respondent 114, via scripts sent to the ICS 110. The Module 208 utilizes questions based upon age, gender, and respondent-specified pathologic conditions. The computer makes use of extensive logic to present questions to the individual respondent that are relevant to gender, age, and health condition. In this manner, large bodies of queries about pathophysiologic function, family history, medications, health habits, health screening, and functional health are excluded. Therefore, the respondent is presented with an extremely efficient series of questions that are tailored to their specific health needs and concerns. The POVC 100 Modules are designed to emulate the logic that a physician might use to gather information about a patient's condition through the physician's formal interview process.

For example, The logic of the Personal Clinical Data analysis module 208 makes extensive use of the then-current nationally accepted guidelines and recommendations for age, gender, and condition specific care. The logic tables can be updated to reflect new nationally accepted guidelines and recommendations periodically.

Data collected is immediately analyzed by the Personal Clinical Data analysis module 208 and can be presented to the respondent/participant for use in the therapeutic interaction with a clinician. The Personal Clinical Data analysis module 208 tailors the data collection and data presentation to the needs and specific situation of a particular respondent, such that the output is a reasonable surrogate for a clinician's typical patient family and social history, review of health habits, review of systems, health concerns, and medication review. The Personal Clinical Data analysis module 208 presents the results of the survey in a manner similar to that a clinician would use in collating data from a patient for use the therapeutic interaction with a patient. In this manner, the POVS provides an extremely time efficient manner of collecting data in a systematic fashion for the clinician. In addition, data are presented with recommendations for action using the then-current nationally accepted guidelines and recommendations for age, gender, and condition specific care. The clinician can review the output with the respondent, and focus attention on the needs and concerns of the respondent in a structured dialogue instead of spending the bulk of time collecting data. The logic of Module 208 are useful for health screening situations.

If the respondent has completed the survey within a certain period of time, six months for example, the system may request that the respondent provide updated information, print reports, and/or send reports to a third party. This ensures that information is kept up to date.

Clinicians, third party payers, and other end users (survey consumers 120) can use the Personal Clinical Data Analysis module 208 to provide individual measurements of pathophysiological functions. Data can be presented to an end user via the Module 208 reporting function, or through the Physician Office Data Presentation Module 220. In addition, data can be aggregated and analyzed. For example, a clinician can use the Personal Clinical Data analysis module 208 to gain information useful in understanding the performance of a collection of patients within a certain age, gender, of specified condition. A third party payer could use the program to screen health plan members for individuals at high risk for developing a condition or having health problems, and place that individual in a preventive health program.

Data checking occurs at time of data collection—the Personal Clinical Data Analysis module 208 does not accept data that is incompatible with the database. Data are stored in the Comparative Practice Data Repository 210 and compared to the Historical Data Repository on Clinic Performance 212. It is possible to store and analyze the responses from millions of respondents. Data are analyzed for content items, data integrity, and completeness. Data are analyzed by the Clinical Data analysis module 208 at storage and when called for display.

The Personal Clinical Data analysis module 208 stores data to and uses data from the Comparative Practice Data Repository 210. The Module 208 also accesses the Clinical Pathophysiologic Normative Data Repository 214 for comparative analysis.

Examples of how the Personal Clinical Data analysis module 208 would be used in various populations of survey participants are given below:

a. Used by an Individual

Individual hears about "QDMHealthLine.com" and logs on to the web site or—

Individual goes to practice and gets handed a PDA with a touch screen data entry capability Individual answers a few questions, selects a UserID and password to his/her personal "health web page"

Individual answers questions, skips some to answer at a later date with more complete data Individual views and prints their Initial "Personal Compass viewpoint"

Individual views and prints the "Health Action Form" (HAF)

Individual gets comparative data on where they are in health status relative their peers Individual stores and retrieves info in a "Health Bank"

Individual clicks on hyperlinks to web sites for more information on conditions/habits in which they are interested, and signs up for the automated search engine to daily load their Personal Web page with new disease, age, and gender specific information Individual specifies to whom the PCVC reports and Health Action Forms will be e-mailed or faxed Individual may sign up for user groups/user forums/and/or mailing lists for areas of which the individual has an interest.

Individual may revisit the form and update certain data at any time b. Used by a Physician Group i) Individual docs not Using the PCVC/POC System Doc logs on to e-mail, sees a PCVC and Health Action Form (HAF) in his/her email box for a patient who will be visiting him/her soon downloads to printer and files in patient chart or—

Doc gets fax from respondent who has taken the survey and wanted it faxed to the doctor for use in the patient—physician therapeutic interaction ii) Physician Offices Using the PCVC/POC System Steps same as individual use above HAF and PVC are printed and given to patient to review The clinical and patient review the HAF and PVC together in the clinical interaction The clinical and Patient make a plan based upon information discussed at the time of care c. Case Management in Third Party Claims Administrators (TPAs), ERISA Exempt Employer Health Plans, Health Plans, and other Managers of Risk.

The Patient PCVC can assist the Case Manager in case and care management, or help the individual manage his/her own care processes and outcomes.

Case Management is defined by the Case Management Society of America as:

A collaborative process which assesses, plans, implements, coordinates, monitors, and evaluates options and services to meet an individual's health needs through communications and available resources to promote quality cost-effective outcomes.

Case management involves the timely coordination of quality healthcare services to meet an individual's specific healthcare needs in a cost-effective manner.

The case manager educates the patient and all members of the healthcare delivery team about case management, community resources, insurance benefits, cost factors, and issues in all related topics so that informed decisions may be made. The case manager is the link between the individual, the providers, the payer, and the community. The case manager should encourage appropriate use of medical facilities and services, improve quality of care, and maintain cost effectiveness on a case—by—case basis.

The case manager collaborates with clients by assessing, facilitating, planning, and advocating for health needs on an individual basis. QDM is in a unique position to help the case manger through its novel and breakthrough technology.

The Case manager uses the PCVC to manage groups of patients with similar disease.

The PCVC is used as follows:

The case manager identifies a person at risk for high cost/problem prone/high risk disease with the likelihood of poor outcome (either by self identification, or through standard means used by health insurance and management companies.)

Patient gives access to the PCVC to the case manager

Patient and case managers together complete the PCVC in some instances.

Patient and case manager decide on a course of actions for maximal health management and outcomes using best practices, the health action form, and the disease-specific forums The case manager receives periodic reports of the patient's progress over the Internet and reviews the progress periodically with the patient.

Case manager may intervene with higher level medical interventions if needed (for example, facilitation a visit to a health care provider, or scheduling a home care nurse).

The case management function of the PCVC is estimated to broaden the scope of patient management by case managers by at least 4 fold.

See: Case Management Society of America. Standards of Practice. Little Rock, Ak. 1995, for more information (incorporated herein by reference).

Figure 5:
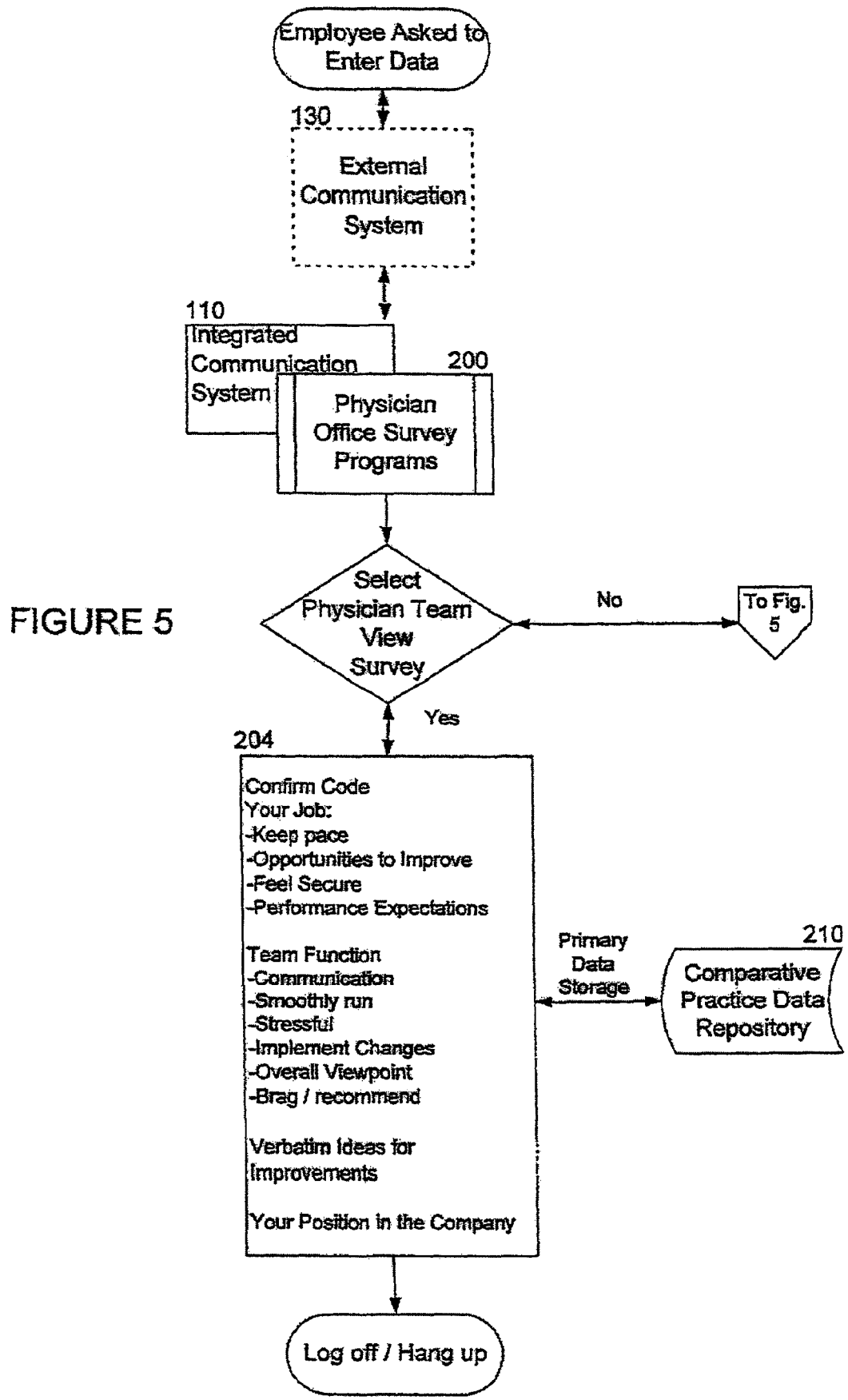
FIG. 5 is a block diagram showing an example of the major functionality and interfaces of the Office Team Viewpoint Module.

FIG. 5 shows the operation of the Office Team Viewpoint Survey Module 204. This module is used to collect and assess information about employees of the office, and their job performance and satisfaction. Workers at a site of care use the Office Team Viewpoint Survey Module 204 to collect data on their opinions about the work environment. It would also be possible to allow workers to access the Module via an External Communication System [ECS] 112 or 130, utilizing the ICS 110. In that case, the Module 204 would provide the scripts for execution on the ICS 110. If internal access is provided so that no ECS is necessary, another platform may provide the execution environment for the Module 204 scripts.

The Module 204 can assess two or more aspects (or domains) of the work environment, such as an individual worker's job function (the domain called "Your Job" in the survey), and the efficiency of teamwork (the domain called "Team Function" in the survey), for example. In worker job function, the Module 204 assesses the worker's feelings about individual job performance and expectations. In team function, the Module 204 assesses how well the work group performs as a team. Verbatim comments are collected about the worker's overall viewpoint, and ideas for improvements at the work site. Basic demographic data is collected as well. The Office Team Viewpoint then thanks the respondent and terminates the interview.

Individual workers might access the Office Team Viewpoint Module 204 using an external connection device (112 or 130), such as the telephone or the Internet, and would thus access the Office Team Viewpoint through the ICS 110. In this implementation, the respondent need not be in the site of work nor need to be near the data collection device. The data collection device could be made available to collect data 24 hours a day, 7 days a week, 365 days a year in an automated fashion. The Office Team Viewpoint Module 204 can be configured to collect data anonymously. The Module 204 program presents questions to the respondent in a sequential fashion using internal logic about the most relevant questions for the individual respondent in the two domains of their work environment. The Module 204 can be set to collect higher level domain data by asking questions that are most predictive of a respondent's opinions, or can be set to "drill down" into the domain to a high degree of specificity before collecting verbatim comments. The triggering event for "drill down" questions is variable, and can be set by the survey programmer in conjunction with the client at the time of design. The program, therefore, can collect relevant domain data rather quickly and efficiently (for example, completing the survey in less than three minutes), or it can collect drill down data and verbatim comments that take the respondent a longer time to complete. Data collected in such a manner yields information of higher sensitivity and specificity and hence greater predictive value. Both brief and comprehensive data collection modalities can be called randomly and run simultaneously on the system. The drill-down methodology applied to a survey process is discussed in the co-pending application Interactive Survey and Data Management Method and Apparatus, Ser. No. 09/871,279 incorporated herein by reference.

Figure 8:
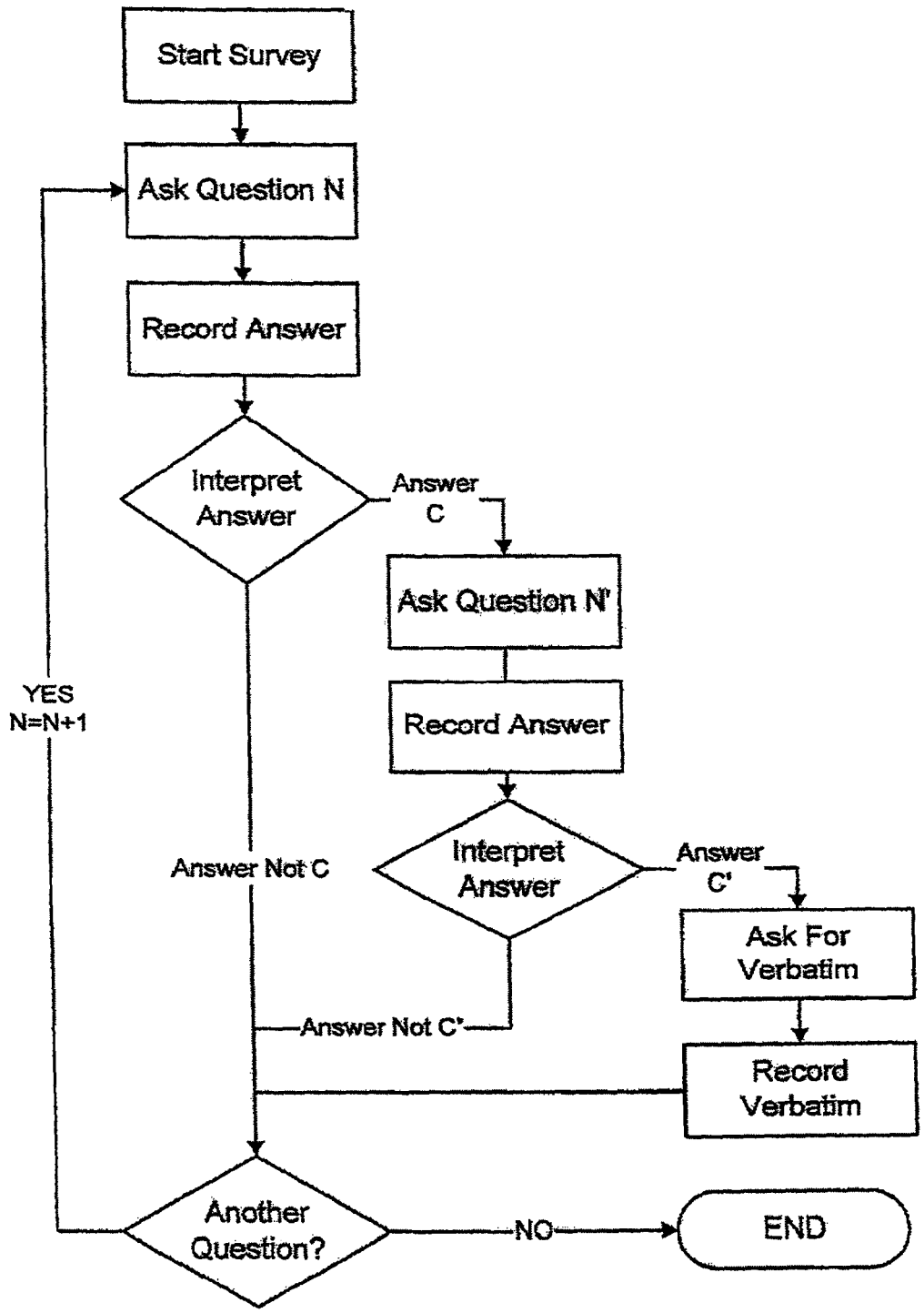
FIG. 8 is a flow chart showing a generic example of Drill-Down Questioning.

FIG. 8 is a flow chart showing a simple example of the interactive survey script approach, wherein focus or drill down surveys containing "drill-down" questions, and open-ended questions called "verbatims", are deployed by the survey. The questions can be pre-determined, but this survey format allows the questioning to "drill-down" into greater detailed questions when certain specific responses are given. As shown in FIG. 8, it may be that answers A and B of question N are of sufficient detail for survey analysis, such that no additional questioning on that specific topic is necessary, while answer "C" requires specific follow-up questioning (i.e., N') to get greater detail on the reasons for the answer "C", for example. Thus, only if the participant answers "C" to question N is question N' asked next. If the participant answers C' to question N', then the participant could be asked to leave a detailed "verbatim" response to explain his or her answer, while answers A' and B' to question N' might require no verbatim. The survey can then go on to the next normal question, N+1.

Using these "drill-down" question techniques, the survey can be "customized" according to the actual responses of the participant, or the participants personal information or medical condition. Multiple variations and levels of drill-down questioning are possible, depending on the purpose of the survey. This capability allows a survey to gather greater detail in those subject areas where a survey consumer might want greater detail, while conserving resources by only asking for that detail when appropriate. The drill-down format could go quite deep into a subject area before requiring a verbatim, or it may only go down a layer or two as shown in FIG. 8. Drill-down questioning is discussed in co-pending application Interactive Survey And Data Management Method And Apparatus, Nelson et al., Ser. No. 09/871,279 incorporated herein by reference. This application is also related to provisional application Ser. No. 60/245,753 and 60/245,769, incorporated herein by reference.

A specific example of how the invention can be used in an employee process improvement program is given below:

Employee Improvement Program Example

Employer makes the Office Team Viewpoint survey available to the workers

Workers log on and complete the survey

Data is reviewed by individual workers about where they compare to their peers on Job efficacy and Team function The manager reviews data in aggregate Manager sees that there are low scores in team Communication domain (for example) when compared to a peer comparison group.

Manager reviews verbatim comments and determines from the verbatim comments that workers would like weekly communication in person from the manager.

Manager adopts an improvement plan for communication and implements it

In the ensuing weeks, manager checks the progress of the workers evaluation of "Team Communication" by weekly reviewing weekly survey results and verbatim comments.

Data checking is performed by the Office Team Viewpoint Module 204 at the time of data collection—the program for storage does not accept data that is incompatible with the database. Data are stored in the Comparative Practice Data Repository 210 and compared to the Historical Data Repository on Clinic Performance 212. It is possible to store and analyze the responses from millions of respondents. Data are analyzed for content items, data integrity, and completeness.

Data are analyzed by the Program at storage and when called for display. Normalized summaries and comparisons between various units and departments, and information about specific types (or classes) of employees can be obtained as desired.

Figure 6:
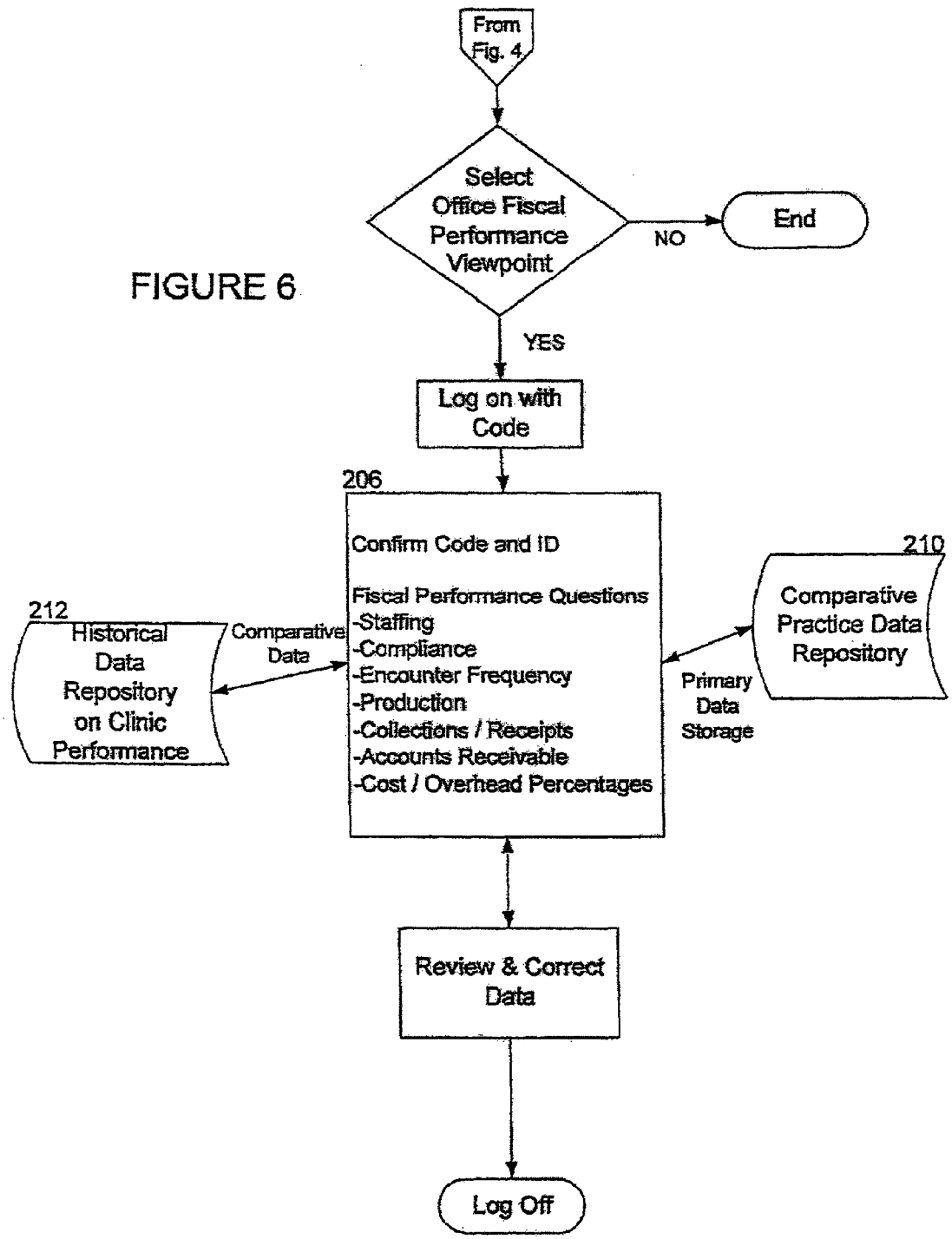
FIG. 6 is a block diagram showing an example of the major functionality and interfaces of the Office Fiscal Performance Module.

FIG. 6 shows the operation of the Office Fiscal Performance Viewpoint Survey Module 206. The "respondent" in this case is typically a manager of a clinic who logs on to the ICS remotely with a connection device such as a telephone or an Internet accessible computer. The Office Fiscal Performance Viewpoint survey program verifies that the respondent has authority to report data, and calls from its database the respondent's demographic data—for example, the type of clinic and number of providers in practice. After respondent verification of demographic data, the ICS 110 initiates the Office Fiscal Performance Viewpoint Survey Module 206, and places the respondent at the beginning of the program. The Office Fiscal Performance Viewpoint Survey Module 206 collects data on office fiscal performance relevant for comparison from past performance and comparison to a historical and real-time cohort of similar providers.

The Office Fiscal Performance Viewpoint Survey Module 206 collects data on staffing ratios, compliance planning and implementation, on patient encounter frequency, on production of providers, on collections and receivables, on billing performance with accounts receivable, and on cost and overhead performance. The respondent can review data and correct it before submission.

Data integrity is checked by the Office Fiscal Performance Viewpoint Survey Module 206 in real-time or near real-time. Data checking occurs at time of data collection—the program for storage does not accept data that is incompatible with the database. Data are stored in the Comparative Practice Data Repository 210 and compared to the Historical Data Repository on Clinic Performance 212. It is possible to store and analyze the responses from millions of respondents. Data are analyzed for content items, data integrity, and completeness. Data are analyzed by the Program at storage and when called for display. Normalized summaries and comparisons between various units and departments, and information about specific types (or classes) of practices can be obtained as desired.

Figure 7:
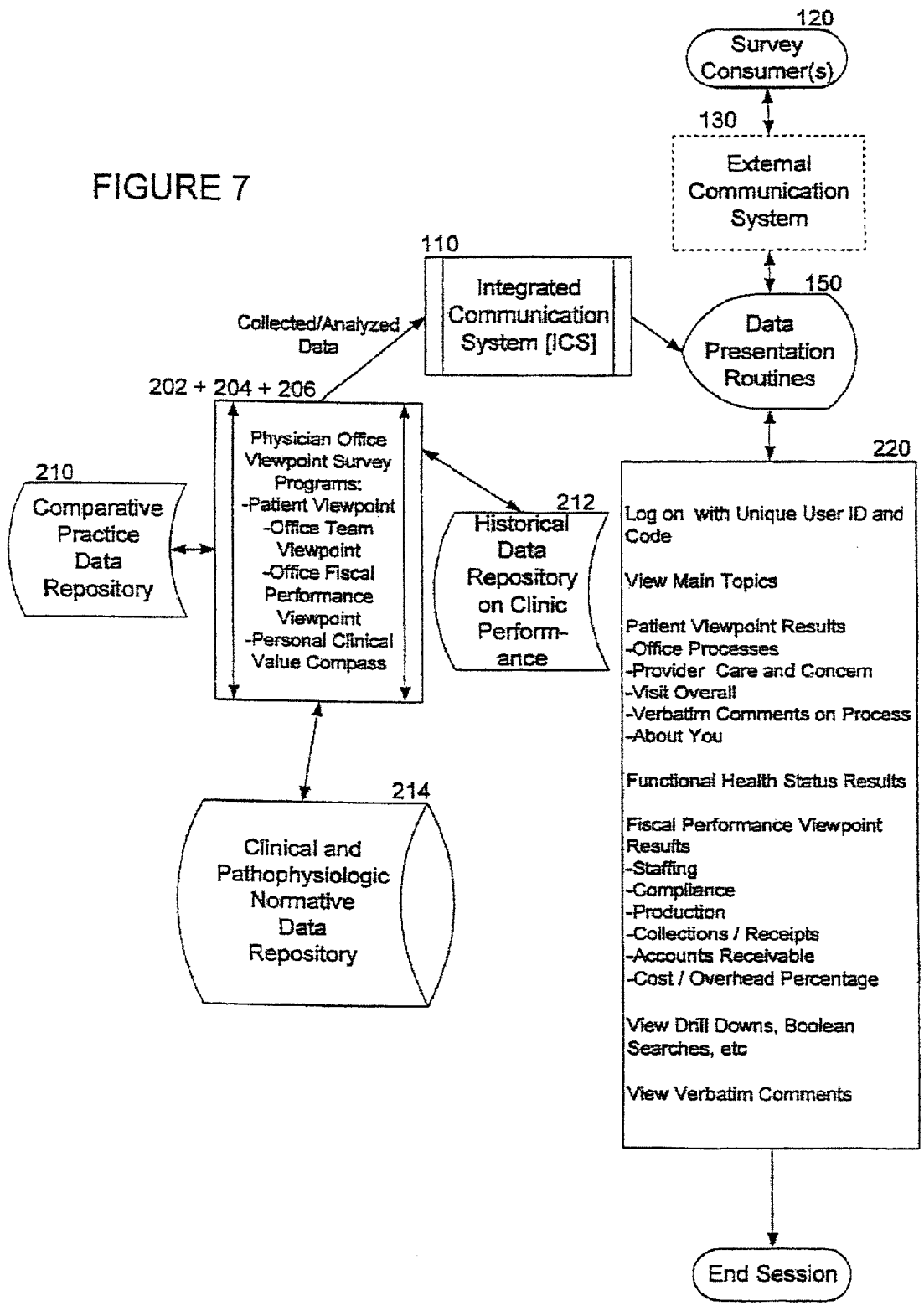
FIG. 7 is a block diagram showing an example of the major functionality and interfaces of the Data Presentation Module.

FIG. 7 shows the operation of the Physician Office Data Presentation Module 220. The Module 220 is the display program for the collected data. Data collected in the Physician Office Viewpoint Survey family are analyzed for display at time of collection and stored in one of three databases. The consumer can be access data remotely through the ICS and an external connection device (such as a telephone, or Internet accessible computer) for reports and analysis. The ICS authenticates the consumer end user, allows or denies access to the data, encrypts and then de-encrypts data as it is transferred to the consumers data reporting device to ensure security and privacy. The consumer can use a remote networking protocol such as the Virtual Private Network (VPN) to report data. A VPN keeps data off of the public Internet and thus enhances data security and privacy. Alternatively, the consumer can use the Internet with standard security measures to ensure data privacy and security. Reports are available 24 hours a day, 7 days a week, 365 days a year. Data are available virtually at the time of collection. The ICS 110 authenticates the consumer and assigns to the consumer the appropriate level of authority to review data.

The Physician Office Data Presentation Module 220 calls the ICS 110 Data Presentation Routines, which access the Physicians Office Viewpoint Survey Modules and Databases. The ICS 110 provides the platform to implement the clinical improvement process and compass viewpoint data presentation paradigm. The databases are preferably relational databases, and as such, can be sorted and presented in a limitless number of ways as directed by the survey consumer or the Modules. The Physician Office Data Presentation Module 220 uses a standard format for presenting data that follows the care process. Data may be viewed in summary (e.g., using a "View Main Topics" category), and the consumer may view the results of any survey—for example, Patient Viewpoint, Functional Health, and Fiscal performance—in specific fashion. Data are presented in graphical format to ease interpretation. Numerous different statistical graphs can be used, such as control charts, frequency charts, normative comparisons, etc., according to the type of information that is being displayed or the desires of the consumer on a Quality Desktop™.

Data can be presented in time-sequence order (that is, in the order that a patient would experience a process) and in a fashion that invites the consumer to take action on the data presented (such as highlighting areas of needed improvement or deteriorating performance). Data are presented at the most general summary level first, and then, at the consumer's discretion, the data are sequentially revealed more specifically to yield "drill down" data of greater specificity but less broad in scope. Each domain of data collection can be displayed to the user for review. In addition, verbatim comments are available to be reviewed in aggregate or one at a time. The examples below provide some of the types of information that can be displayed to a user:

Personal Demographics
Age Group
Gender
Provider
Functioning—Team Performance
Your Job
Keep Pace
Use Initiative and improve work
Secure
Clear expectations
Team and Teamwork
Cooperate
Attitudes
Smoothly run
Stressful
Implement changes
Fiscal
Production Days in AR
Net Collection %
Gross Charges
Work RVUs
Biological
Moderate activities
Climbing a flight of stairs
Interfere with normal work
Very nervous
A lot of energy
Down hearted and blue
Overall Health
Satisfaction
Initiating Care—Office Processes
Phone process: getting through to the office
Wait to get appointment
Office wait
Receiving Care—Provider Care
Sensitivity of Staff
Provider Care and Concern
How well provider explained things Provider's thoroughness, carefulness, and technical skills
Amount of time spent with you
Other Aspects of Care
Degree of involvement in decision making
See provider you wanted to see
Problems with asking all of your questions
Verbatims
Best surprise
Worst surprise
How could we improve care to meet your needs
Overall
Overall quality of visit
Overall quality of care and services received Data are presented graphically for use in a balanced scorecard approach known as the "Value Compass" using a "compass viewpoint" presentation paradigm. The compass viewpoint is a data presentation paradigm that presents data from a family of surveys in an integrated, balanced manner utilizing a clinical improvement process so that the consumer can evaluate the performance of various aspects of the clinic and make changes to keep all components in optimal balance. For example, on the compass face for the Physician Office Viewpoint Surveys, Functional Health status can be represented as the North point of the compass, patient satisfaction with office processes, employee job satisfaction, and team function can be represented by the East point of the compass, Fiscal performance by the South point, and Biological function by the West point, using the clinical improvement process and integrative Compass Viewpoint approach to data display. The resulting survey information can be formatted for display in audio, graphical, video, and textual context as appropriate for the type of information displayed. Charts and graphs can be generated from this information when desirable. Examples of screen outputs are given in FIG. 9 and FIG. 10, which show a Health Action Form which can be used by a patient with his or her doctor or health provider to focus on and improve the patient's health. Additional examples of output, and additional information about the clinical improvement process and the compass viewpoint presentation are found in co-pending application Method And System For Presentation Of Survey And Report Data, Ser. No. 10/011,014, incorporated herein by reference.

The POVS can be used in doctors offices, for example, where it is expected to provide immediate utility. Useful information that can be obtained from processing survey data includes, but is not limited to:

(A) generating consumer satisfaction measures such as:
  (i) consumer loyalty measures;
  (ii) medical care satisfaction measures;
  (iii) medical facility satisfaction measures;
  (iv) medical staff satisfaction measures;
  (v) positive comments with reasons; and
  (vi) negative comments with reasons;
(B) generating staff rating measures such as:
  (i) staff loyalty measures;
  (ii) staff performance measures;
  (iii) staff satisfaction measures; and
  (iv) staff continuing education measures;
(C) generating doctor rating measures comprising:
  (i) quality of medical care measures;
  (ii) doctor performance measures;
  (iii) doctor satisfaction measures;
  (iv) doctor loyalty measures; and
  (iv) doctor continuing education measures;
(D) generating care delivery measures such as:
  (i) cost measures including:
    (a) cost of medical care paid by consumer measures;
    (b) cost of medical care paid by non-consumer measures;
    (c) cost of providing medical care measures; and
    (d) overhead costs measures;
  and
  (ii) profit measures;
(E) generating medical care quality assessment measures such as:
  (i) mortality measures
  (ii) morbidity measures;
  (iii) complications measures;
  (iv) medical procedure results measures;
  (iv) medical procedure follow-up measures;
  (vi) patient mental health measures;
  (vii) social impact measures;
  (viii) hospital stay length measures;
  (ix) HEDIS® technical quality measures; and
  (x) PM PM cost measures;
(F) analyzing the generated measures and survey data, such as:
  (i) aggregating survey data to form assessments;
  (ii) normalizing comparisons between specific named units including:
    (a) doctors or specialists;
    (b) medical care organizations or divisions;
    (c) staff persons;
    (d) managers;
    (e) specific medical treatments; and
    (f) patient group status;
  (iii) determining changes over time;
  (iv) determining differences geographically; and
  (v) generating summaries.

As an example in how to utilize the system in a quality improvement program, survey information consumers might want to review their organization's data in an area where a standard survey, implemented by the POVS or some traditional alternative, had identified some performance deficiencies. Focus surveys can be designed and implemented to collect the necessary raw data from the organization's customers and/or staff. The raw survey data is processed, formatted, and made available to the appropriate persons via the POVS, providing useful information and conclusions so that the management of the organization is in a position to better understand the cause of the deficiency and make the proper corrections, thereby improving the quality of goods and/or services and the performance of the organization.

After making changes (to correct the deficiency), focus surveys can be designed and/or performed again to measure the impact of the changes and perhaps fine-tune the results, and to provide continuing assessments of the service provided to patients.

The invention has been described hereinabove using specific examples; however, it will be understood by those skilled in the art that various alternatives may be used and equivalents may be substituted for elements or steps described herein, without deviating from the scope of the invention. Modifications may be necessary to adapt the invention to a particular situation or to particular needs without departing from the scope of the invention. It is intended that the invention not be limited to the particular implementation described herein, but that the claims be given their broadest interpretation to cover all embodiments, literal or equivalent, covered thereby.

The invention claimed is:

1. A system including one or more computers for collecting, processing, and presenting survey information comprising:
   I. an automated survey communication system for connecting to a survey participant and obtaining survey data during a survey, said survey communication system capable of executing software scripts for implementing desired automated survey routines;
   II. a customer viewpoint module implemented by at least one of said one or more computers for providing software scripts to said survey communication system for surveying survey participants who are customers and further for receiving said survey data from said survey communication system, said survey data obtained from the patients including patient viewpoint data;
   III. a personal clinical data analysis module implemented by at least one of said one or more computers for generating analyzed data generated by analyzing said participant survey data, wherein said personal clinical data analysis module generates reports on said analyzed data for use by the survey consumer;
   IV. an office team viewpoint module implemented by at least one of said one or more computers for providing software scripts to said survey communication system for surveying survey participants who are employees and further for receiving said survey data from said survey communication system, said survey data obtained from the employees including employee viewpoint data;
   V. an office fiscal performance viewpoint module implemented by at least one of said one or more computers for providing software scripts to said survey communication system for surveying survey participants who are managers and further for receiving said survey data from said survey communication system, said survey data obtained from the managers including fiscal performance data; and
   VI. an office data presentation module implemented by at least one of said one or more computers for generating assessed survey information for presenting to end users in a formatted manner, said assessed survey information including information for providing quality assessments of an organization, wherein
   said assessed survey information is formatted differently for display to the end user by at least one of said one or more computers depending on whether the end user is a customer or is not a customer, and wherein
   said system is adapted for providing information for displaying assessed survey information to the end user during, or immediately after, said survey.

2. The system according to claim 1 applied to a medical care provider, wherein said customer is a patient, said system further comprising:
   a comparative practice data repository for storing and retrieving said survey data and for storing and retrieving said analyzed data and for storing and retrieving said assessed survey information;
   a historical data repository on clinic performance for storing fiscal historical performance normative data for use by said office data presentation module for generating and displaying historical fiscal performance comparisons for predicting fiscal success; and
   a clinical and pathophysiologic normative data repository for storing clinical and pathophysiologic normative data obtained from various sources, said clinical and pathophysiologic normative data relating patient parameters including age, gender, and medical conditions.

3. The system according to claim 2, wherein said customer viewpoint data includes:
   A. customer satisfaction data;
   B. office process viewpoint data;
   C. provider care and concern data; and
   D. verbatim viewpoint comments;
   and further wherein said employee viewpoint data includes:
      A. job performance data including:
         i. ability to keep pace data;
         ii. opportunities to improve data;
         iii. job security data; and
         iv. performance expectations data;
      B. team function data including:
         i. team communication data;
         ii. team operation data;
         iii. stress environment data;
         iv. change implementation data; and
         v. overall viewpoint data;
      C. verbatim comments; and
      D. employee function data;
   and still further wherein said fiscal performance data includes:
      A. staffing data;
      B. compliance data;
      C. encounter frequency data;
      D. production data;
      E. collections data
      F. receipts data;
      G. accounts receivable data;
      H. cost data; and
      I. overhead data.

4. The system according to claim 3 wherein said analyzed data includes:
   A. comparative patient level data for storing in said clinical and pathophysiological normative data repository, said comparative patient level data including a plurality of the members of the group consisting of:
      i. patient age data;
      ii. patient gender data;
      iii. patient functional health status data
      iv. patient health screening data
      v. patient family medical history data;
      vi. patient medication data;
      vii. patient pathophysiology data;
      viii. patient health habits data;
      ix. patient counseling data;
      x. patient satisfaction data;
      xi. patient health care access data; and
      xii. patient payment capability data;
   B. comparative data for stored in said comparative practice data repository; and
   C. analyzed data stored in said comparative practice data repository.

5. The system according to claim 4 wherein said assessed survey information includes:
   A. patient viewpoint results including:
      i. office process viewpoints;
      ii. provider care and concern viewpoints;
      iii. overall visit viewpoints; and
      iv. verbatim comments on processes;
   B. functional health status results; and
   C. fiscal performance viewpoint results.

6. The system according to claim 1 applied to a medical care provider wherein said customer is a patient and further wherein said analyzed data includes:
- A. comparative patient level data for storing in said clinical and pathophysiological normative data repository, said comparative patient level data including a plurality of the members of the group consisting of:
  - i. patient age data;
  - ii. patient gender data;
  - iii. patient functional health status data
  - iv. patient health screening data
  - v. patient family medical history data;
  - vi. patient medication data;
  - vii. patient pathophysiology data;
  - viii. patient health habits data;
  - ix. patient counseling data;
  - x. patient satisfaction data;
  - xi. patient health care access data; and
  - xii. patient payment capability data;
- B. comparative data for stored in said comparative practice data repository; and
- C. analyzed data stored in said comparative practice data repository.

7. The system according to claim 6 wherein said assessed survey information includes:
- A. patient viewpoint results including:
  - i. office process viewpoints;
  - ii. provider care and concern viewpoints;
  - iii. overall visit viewpoints; and
  - iv. verbatim comments on processes;
- B. functional health status results; and
- C. fiscal performance viewpoint results.

8. The system according to claim 2 applied to a medical care provider, wherein said customer is a patient and further wherein said assessed survey information includes:
- A. patient viewpoint results including:
  - i. office process viewpoints;
  - ii. provider care and concern viewpoints;
  - iii. overall visit viewpoints; and
  - iv. verbatim comments on processes;
- B. functional health status results; and
- C. fiscal performance viewpoint results.

9. The system according to claim 1 applied to a medical care provider wherein said customer is a patient and further wherein said analyzed data includes at least two of the members of the group consisting of:
- patient family and social histories;
- reviews of health habits;
- health concerns;
- medication reviews;
- health screening information; and
- recommendations based on nationally accepted guidelines, age, gender, and condition specific care.

10. A system including one or more computers for collecting, processing, and presenting survey information comprising:
- I. a communication system for connecting to a survey participant over an external communication system;
- II. at least one of said one or more computers being adapted for conducting a plurality of automated surveys with survey participants, said automated surveys being conducted according to survey scripts, said survey scripts providing instructions for conducting said automated survey to collect survey data, said conducting a plurality of automated surveys with survey participants including the steps of:
  - A. conducting a survey with a participant who is a patient according to patient survey scripts including scripts for obtaining survey data including patient viewpoint data;
  - B. conducting a survey with a participant who is an employee according to employee survey scripts including scripts for obtaining survey data including employee viewpoint data; and
  - C. conducting a survey with a participant who is a manager according to manager survey scripts including scripts for obtaining survey data including fiscal performance data;
- III. at least one of said one or more computers being adapted for generating analyzed data from said survey data, wherein said analyzed data utilizes a compass viewpoint information presentation paradigm;
- IV. at least one of said one or more computers being adapted for generating reports utilizing said survey data and said analyzed data, said reports for use by a survey consumer or for use by said survey participant; and
- V. at least one of said one or more computers being adapted for generating assessed survey information from said survey data and said analyzed data, and
- VI. at least one of said one or more computers being adapted for formatting said assessed survey information for display to a survey consumer, wherein said assessed survey information is formatted differently for display to the end user by at least one of said one or more computers depending on whether the end user is a customer or not a customer, and wherein said system is adapted for providing information for displaying assessed survey information to the end user during, or immediately after, said survey.

11. A system for collecting, processing, and presenting survey information, said system comprising:
- an automated survey communication system for connecting to a survey participant over an external communication system, and adapted for conducting a plurality of automated surveys with survey participants for obtaining updated survey data, said conducting a plurality of automated surveys including:
  - conducting a survey with a participant who is a customer to obtain survey data including customer viewpoint data; and
  - conducting a survey with a participant who is not a customer to obtain survey data including viewpoint data including data that is not customer viewpoint data;
- a database for storing the updated survey data,
- the database also for storing historical survey data including data collected and/or analyzed during previous surveys;
- an analysis and presentation subsystem including a computer adapted for analyzing said updated survey data during said conducting a survey to generate analyzed data, and for automatically generating reports utilizing said historical survey data and said analyzed data, said reports provided for use by a survey consumer who is not a customer;
- said analysis and presentation subsystem also adapted for automatically generating display information utilizing at least a portion of said analyzed data, wherein said display information is formatted differently based on whether the participant is a customer or is not a customer;
- said analysis and presentation subsystem also adapted for providing said display information for display to each of said participants during, or immediately thereafter, the conducting of the survey for that participant, for providing feedback to the participants; and said analysis and presentation subsystem also adapted for providing information for displaying said reports to said consumer, said reports being formatted differently than said display information displayed to said participants.

12. The system of claim 11 utilizing a drill-down methodology in said survey, said drill-down methodology utilizing one or both of survey data already provided by the survey participant and/or the historical survey data to determine a subsequent survey question to be asked of the current survey participant.

13. The system of claim 11, wherein said reports are made available immediately after said conducting the survey for each one of the participants.

14. A method for collecting, processing, and presenting survey information using a computer system comprising one or more computers, said method comprising the steps of:
   I. connecting to a survey participant over an external communication system using a survey communication system;
   II. conducting a plurality of automated surveys with survey participants for obtaining updated survey data, said conducting a plurality of automated surveys including the steps of:
      A. conducting a survey with a participant who is a customer to obtain survey data including customer viewpoint data; and
      B. conducting a survey with a participant who is not a customer to obtain survey data including viewpoint data including data that is not customer viewpoint data;
   III. storing the updated survey data in a database;
   IV. storing historical survey data including data collected and/or analyzed during previous surveys in the database;
   V. during said conducting a survey, using the computer system for automatically analyzing said updated survey data to generate analyzed data;
   VI. using the computer system for automatically generating reports utilizing said historical survey data and said analyzed data, said reports provided for use by a survey consumer who is not a customer;
   VII. using the computer system for automatically generating display information utilizing at least a portion of said analyzed data, wherein said display information is formatted differently based on whether the participant is a customer or is not a customer;
   VIII. providing said display information to each of said participants during, or immediately thereafter, the conducting of the survey for that participant, for providing feedback to the participants; and
   IX. providing said reports to said consumer, said reports being formatted differently than said display information provided to said participants.

15. The method of claim 14, utilizing a drill-down methodology in said survey, said drill-down methodology utilizing one or both of survey data already provided by the survey participant and/or the historical survey data to determine a subsequent survey question to be asked of the current survey participant.

16. The method of claim 14, wherein said reports are made available immediately after said conducting the survey for each one of the participants.

17. A method for collecting, processing, and presenting survey information using a computer system comprising one or more computers, said system comprising the steps of:
   I. connecting to a survey participant over an external communication system;
   II. conducting a plurality of automated surveys with survey participants for obtaining survey data, said conducting a plurality of automated surveys including the steps of:
      A. conducting a survey with a participant who is a customer to obtain survey data including customer viewpoint data; and
      B. conducting a survey with a participant who is an employee to obtain survey data including employee viewpoint data;
   III. using the computer system for generating analyzed data from said survey data;
   IV. using the computer system for generating reports utilizing said survey data and said analyzed data, said reports for use by a survey consumer;
   V. using the computer system for generating assessed survey information from said survey data and said analyzed data;
   VI. using the computer system for formatting said assessed survey information for display to a survey consumer; and
   VII. using the computer system for generating, formatting, and providing information for displaying a formatted survey report incorporating survey data obtained from the current participant in real time or near real time, utilizing historical survey data, to each survey participant during each of said surveys, said survey results formatted for being displayed in a customized manner based on whether the current survey participant is a customer or not a customer.

18. The method according to claim 17, wherein said conducting a plurality of automated surveys includes the step of conducting a survey with a participant who is a manager to obtain survey data including fiscal performance data.

19. The method according to claim 18, wherein said customer viewpoint data includes:
   A. customer satisfaction data;
   B. office process viewpoint data;
   C. provider care and concern data; and
   D. verbatim viewpoint comments;
and further wherein said employee viewpoint data includes:
   A. job performance data including:
      i. ability to keep pace data;
      ii. opportunities to improve data;
      iii. job security data; and
      iv. performance expectations data;
   B. team function data including:
      i. team communication data;
      ii. team operation data;
      iii. stress environment data;
      iv. change implementation data; and
      v. overall viewpoint data;
   C. verbatim comments; and
   D. employee function data;
and still further wherein said fiscal performance data includes:
   A. staffing data;
   B. compliance data;
   C. encounter frequency data;
   D. production data;
   E. collections data
   F. receipts data;
   G. accounts receivable data;
   H. cost data; and
   I. overhead data.

20. The method according to claim 19 as applied to a medical care facility, wherein said customer is a patient, and further wherein said analyzed data includes:
A. comparative patient level data including:
i. patient age data;
ii. patient gender data;
iii. patient functional health status data
iv. patient health screening data
v. patient family medical history data;
vi. patient medication data;
vii. patient pathophysiology data;
viii. patient health habits data;
ix. patient counseling data;
x. patient satisfaction data;
xi. patient health care access data; and
xii. patient payment capability data.

21. The method according to claim 20, wherein said assessed survey information includes:
A. patient viewpoint results including:
i. office process viewpoints;
ii. provider care and concern viewpoints;
iii. overall visit viewpoints; and
iv. verbatim comments on processes;
B. functional health status results; and
C. fiscal performance viewpoint results.

22. The method according to claim 21, wherein said formatting said assessed survey information is done according to a compass viewpoint information presentation paradigm.

23. The method according to claim 18 applied to a medical care provider wherein said customer is a patient and further wherein said analyzed data includes:
A. comparative patient level data including:
i. patient age data;
ii. patient gender data;
iii. patient functional health status data
iv. patient health screening data
v. patient family medical history data;
vi. patient medication data;
vii. patient pathophysiology data;
viii. patient health habits data;
ix. patient counseling data;
x. patient satisfaction data;
xi. patient health care access data; and
xii. patient payment capability data.

24. The method according to claim 23, wherein said assessed survey information includes:
A. patient viewpoint results including:
i. office process viewpoints;
ii. provider care and concern viewpoints;
iii. overall visit viewpoints; and
iv. verbatim comments on processes;
B. functional health status results; and
C. fiscal performance viewpoint results.

25. The method according to claim 24, wherein said formatting said assessed survey information is done according to a compass viewpoint information presentation paradigm.

26. The method according to claim 18 wherein:
A. said automated surveys are conducted according to survey scripts and said survey scripts provide instructions for conducting said automated survey to collect survey data;
B. conducting said survey with a participant who is a customer is conducted according to customer survey scripts including scripts for obtaining survey data including customer viewpoint data;
C. conducting said survey with a participant who is an employee is conducted according to employee survey scripts including scripts for obtaining survey data including employee viewpoint data; and
D. conducting said survey with a participant who is a manager is conducted according to manager survey scripts including scripts for obtaining survey data including fiscal performance data;
E. said analyzed data utilizes a compass viewpoint information presentation paradigm;
F. said reports for use by a survey consumer are for use by a survey consumer or for use by said survey participant;
G. said generating assessed survey information from said survey data and said analyzed data is in real time or near real time; and
H. said formatting said assessed survey information is into a formatted survey report and said display to a survey consumer is during or immediately after any of said surveys.

27. The method according to claim 17 wherein:
A. said conducting a plurality of automated surveys is conducted using said external communication system and said conducting a plurality of automated surveys uses a drill-down methodology;
B. said generating reports utilizing said survey data and said analyzed data is conducted using the computer system;
C. said generating assessed survey information form said survey data and said analyzed data is conducted using the computer system;
D. said formatting said assessed survey information for display to a survey consumer is conducted using the computer system
E. said generating, formatting, and displaying derivative survey information is conducted using the computer system, wherein
said drill-down methodology utilizes one or both of survey data already provided by the survey participant and historical survey data to determine a subsequent survey question to be asked of the current survey participant.

28. The method of claim 27, wherein said assessed survey information is presented in seconds.

* * * * *

UNITED STATES PATENT AND TRADEMARK OFFICE
CERTIFICATE OF CORRECTION

PATENT NO.           : 8,489,414 B2
APPLICATION NO.      : 12/394659
DATED                : July 16, 2013
INVENTOR(S)          : J. Edward McEachern It is certified that error appears in the above-identified patent and that said Letters Patent is hereby corrected as shown below:

In the Specification:

Column 1, Line 66, "Ser. No. 19/911,915," should read -- Ser. No. 10/011,014, --

Column 11, Line 54, "1> Excellent" should read -- <1> Excellent --

Column 12, Line 8, "1> Excellent" should read -- <1> Excellent --

Signed and Sealed this
Tenth Day of September, 2013

Teresa Stanek Rea
*Acting Director of the United States Patent and Trademark Office*